United States Patent
Boeke et al.

(10) Patent No.: US 9,631,204 B2
(45) Date of Patent: Apr. 25, 2017

(54) VERSATILE GENETIC ASSEMBLY SYSTEM (VEGAS) TO ASSEMBLE PATHWAYS FOR EXPRESSION

(71) Applicants: New York University, New York, NY (US); John Hopkins University, Baltimore, MD (US)

(72) Inventors: Jef Boeke, New York, NY (US); Leslie Mitchell, New York, NY (US); Yizhi Cai, Edinburgh (GB); Neta Agmon, New York, NY (US)

(73) Assignees: New York University, New York, NY (US); Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/742,210

(22) Filed: Jun. 17, 2015

(65) Prior Publication Data
US 2016/0046972 A1    Feb. 18, 2016

Related U.S. Application Data

(60) Provisional application No. 62/013,321, filed on Jun. 17, 2014.

(51) Int. Cl.
*C12N 15/64* (2006.01)
*C12N 15/90* (2006.01)
*C12N 15/10* (2006.01)
*C12N 15/66* (2006.01)

(52) U.S. Cl.
CPC .......... *C12N 15/902* (2013.01); *C12N 15/10* (2013.01); *C12N 15/64* (2013.01); *C12N 15/66* (2013.01)

(58) Field of Classification Search
None
See application file for complete search history.

(56) References Cited

PUBLICATIONS

Weber et al., PLoS ONE, vol. 6 (2011) pp. 1-11.*
Gibson et al., Proc. Natl. Acad. Sci., vol. 105 (2008) pp. 20404-20409.*

* cited by examiner

*Primary Examiner* — Jim Ketter
(74) *Attorney, Agent, or Firm* — Hodgson Russ LLP

(57) ABSTRACT

Provided are compositions and methods for use in assembling and expressing a plurality of transcription units using, in one aspect, homologous recombination in yeast. Yeast containing the plurality of transcription units, and isolated transcription units, are also provided. Kits for use in making the yeast and the transcript units are further included.

11 Claims, 13 Drawing Sheets
(13 of 13 Drawing Sheet(s) Filed in Color)

VERSATILE GENETIC ASSEMBLY SYSTEM (VEGAS) TO ASSEMBLE PATHWAYS FOR EXPRESSION

CROSS-REFERENCE TO RELATED APPLICATIONS

This application claims priority to U.S. Provisional patent application No. 62/013,321, filed Jun. 17, 2014, the disclosure of which is incorporated herein by reference.

STATEMENT REGARDING FEDERALLY SPONSORED RESEARCH

This invention was made with government support under contract no. MCB-0718846 awarded by National Science Foundation and under contract no. N66001-12-C-4020 awarded by the Defense Advanced Research Projects Agency. The government has certain rights in the invention.

BACKGROUND OF THE DISCLOSURE

*S. cerevisiae* is a prominent model organism and a highly valued chassis in the field of synthetic biology. In this space, metabolic engineering is a major focus, as the expression of one or more heterologous enzymes can transform *S. cerevisiae* into a tiny cellular factory. The most well-known example of this to date is the engineering of *S. cerevisiae* to produce commercially relevant concentrations of artemisinic acid, a precursor to the anti-malarial drug artemisinin. These metabolic engineering projects require both the introduction of heterologous genes whose expression levels are finely tuned, and the redirection of endogenous biosynthetic pathways via modification of native genes. The development of tools to aid in construction and manipulation of both native and non-native genes for expression in *S. cerevisiae* thus facilitates metabolic engineering and synthetic biology in yeast.

Typical yeast protein coding genes have a relatively simple anatomy, due in part to the compact structure of the *S. cerevisiae* genome. Promoters are short, generally extending only ~500 bp upstream of the start codon. Only ~20% of promoters in the yeast genome contain TATA boxes. On average, native coding sequences (CDS) are ~1 kb long and less than 5% contain introns. Sequences associated with 3' end formation, which typically extend ~200 bp downstream of the stop codon, are usually AT-rich and contain information for both transcriptional termination and 3' end processing. The simple structure of yeast genes means that expression of non-native proteins in yeast can be achieved by encoding the CDS of interest between a promoter and terminator that can function in *S. cerevisiae*. Tuning of CDS expression level can then be accomplished by varying the promoter and terminator sequences, changing the gene copy number (e.g. high or low copy plasmid), or altering the genomic locus in which the gene is integrated.

The production of high-value metabolites in microorganisms suited to industrial scale growth can overcome costly issues associated with traditional production routes, including yield, extraction, or complicated synthesis procedures. To achieve this, the biosynthetic pathway of interest must be re-constructed in an appropriate host organism, typically chosen because it is well characterized and genetically tractable. *Saccharomyces cerevisiae* is a favored eukaryotic microorganism for metabolic engineering because it is industrially robust, generally regarded as safe, and highly amenable to and tolerant of genetic manipulation. Many recent successes in the metabolic engineering of *S. cerevisiae* have been described, most notably the cost-effective production of artemisinic acid, a precursor to the anti-malarial drug artemisinin. Engineering of the host genome to redirect endogenous pathways and optimizing the expression levels of non-native biosynthetic genes are keys to successful metabolic engineering projects. However, there remain significant challenges to efficiently assembling biosynthetic pathways and other gene sets for expression in *S. cerevisiae*. The present disclosure meets these and other challenges.

SUMMARY OF THE DISCLOSURE

The present disclosure comprises compositions and methods for assembling genetic pathways for expression in *S. cerevisiae*. The pathway assembly method, called VEGAS (Versatile Genetic Assembly System), exploits the native capacity of *S. cerevisiae* to perform homologous recombination and efficiently join sequences with terminal homology. Terminal homology between adjacent pathway genes and an assembly vector is encoded by 'VEGAS adapter' (VA) sequences, which are orthogonal in sequence with respect to the yeast genome. Prior to pathway assembly by VEGAS in *S. cerevisiae*, each gene is assigned an appropriate pair of VAs and assembled using a technique called yeast Golden Gate (yGG). The VEGAS improvement enables building a plurality of transcription units (TUs). We demonstrate the assembly of four, five, and six gene pathways by VEGAS to generate *S. cerevisiae* cells synthesizing β-carotene and violacein. Moreover, we demonstrate the capacity of the VEGAS approach for combinatorial assembly. Thus, the disclosure in various embodiments encompasses compositions and methods for making recombinant vectors suitable for homologous recombination with each other in yeast.

In an embodiment the disclosure provides a method comprising: i) providing a first recombinant vector (CDS vector) comprising a protein coding sequence (CDS sequence) wherein the CDS is flanked on its 5' and 3' ends by first Type IIS restriction enzyme recognition sites, the CDS vector further comprising a first antibiotic resistance gene; ii) providing a second recombinant vector (PRO vector) comprising a promoter sequence (PRO sequence) wherein the PRO sequence is flanked on its 5' and 3' ends by the first Type IIS restriction enzyme recognition sites, the PRO vector further comprising the first antibiotic resistance gene; iii) providing a third recombinant vector (TER vector) comprising a transcription termination sequence (TER sequence) wherein the TER sequence is flanked on its 5' and 3' ends by the first restriction Type IIS enzyme recognition sites, the TER vector further comprising the first antibiotic resistance gene; iv) providing a fourth recombinant vector (LVA vector) comprising a first left adapter polynucleotide sequence (LVA sequence) wherein the LVA sequence is flanked on its 5' and 3' ends by the first Type IIS restriction enzyme recognition sites, the LVA vector further comprising the first antibiotic resistance gene; v) providing a fifth recombinant vector (RVA vector) comprising a first right adapter polynucleotide sequence (RVA sequence) wherein the RVA sequence is flanked on its 5' and 3' ends by the first Type IIS restriction enzyme recognition sites, the RVA vector further comprising the first antibiotic resistance gene; vi) providing a sixth recombinant vector (acceptor vector) comprising a segment, the segment comprising a polynucleotide sequence encoding a detectable marker (detectable marker sequence), wherein the detectable marker sequence is flanked by the first Type IIS restriction enzyme recognition sites, and wherein the segment is flanked by a second Type IIS restriction enzyme recognition sites, wherein the acceptor vector comprises a second antibiotic resistance gene but does not comprise the first antibiotic resistance gene; vii) incubating the CDS vector, the PRO vector, the TER vector, the LVA vector, the RVA vector, and the acceptor vector in a single reaction container with a first Type IIS restriction endonuclease that recognizes the first Type IIS restriction endonuclease recognition site and a DNA ligase enzyme such that ligated vectors are produced, wherein the ligated vectors comprise sequentially the LVA sequence, the PRO sequence, the CDS sequence, the TER sequence, and the RVA sequence (LVA-TU-RVA vectors), wherein the PRO, CDS and TER sequences comprise a transcription unit (TU), and wherein the LVA-TU-RVA vectors comprise the second antibiotic resistance gene, but do not comprise the first antibiotic resistance gene, wherein the LVA-TU-RVA vectors do not comprise the detectable marker sequence, and wherein the ligated vectors do not comprise the first Type IIS restriction site, but do comprise the second Type IIS restriction site; viii) introducing the LVA-TU-RVA vectors from vii) into bacteria and culturing the bacteria with a culture medium comprising an antibiotic to which bacteria comprising the LVA-TU-RVA vectors are resistant via expression of the second antibiotic resistance gene such that clonal colonies of the bacteria comprising the VEGAS vectors are formed, wherein the clonal colonies do not express the detectable marker; and viii) isolating the LVA-TU-RVA vectors from the colonies that do not express the detectable marker to obtain isolated LVA-TU-RVA vectors. In embodiments, certain steps of the method are performed using PCR. In certain embodiments, the CDS sequence comprises on its 5' end the sequence: AATG and at its 3' end the sequence TGAG; and/or the PRO sequence comprises at its 5' end the sequence: CAGT and at its 3' end the sequence AATG; and/or the TER sequence comprises at its 5' end the sequence TGAG and at its 3' end the sequence TTTT; and/or the LVA sequence comprises at its 5' end the sequence CCTG and at its 3' end the sequence CAGT; and/or the RVA sequence comprises at its 5' end TTTT and at its 3' end the sequence AACT; and/or the detectable marker sequence comprises at its 5' end the sequence CCTG and at its 3' end the sequence AACT.

In certain embodiments, the disclosure includes a first LVA sequence that comprises or consists of the sequence: CCCCTTAGGTTGCAAATGCTCCGTCGACGGGATCT-GTCCTTCTCTGCCGGCGATCGT (SEQ ID NO:1) (VA1*). In certain embodiments, the disclosure includes a first RVA sequence that comprises or consists of the sequence:

(VA2**)
(SEQ ID NO: 2)
TGACGCTTGGATGCGTGACCCCGTACGTCATGACCCGTCATGGGTATG
TAAGCGAAG.

In an aspect of the disclosure a method for producing a homologously recombined DNA molecule comprising distinct transcription units (TU) is provided. This generally comprises: i) providing a plurality of LVA-TU-RVA vectors obtained as described above, wherein each LVA-TU-RVA vector in the plurality comprises a distinct TU that comprises a distinct CDS, and wherein each LVA-TU-RVA vector further comprises an LVA sequence and an RVA sequence, wherein only one LVA-TU-RVA vector in the plurality comprises a first LVA sequence (VA1 sequence) that is identical to a first LVA sequence in a yeast VEGAS acceptor vector, and wherein only one LVA-TU-RVA vector in the plurality comprises a first RVA sequence (VA2 sequence) that is identical to a first RVA sequence in the yeast VEGAS acceptor vector. The method further comprises ii) linearizing the plurality of LVA-TU-RVA vectors by digestion with a Type IIS restriction enzyme to obtain distinct linearized LVA-TU-RVA vector fragments that comprise the distinct TUs, and sequentially or concurrently iii) providing a linearized yeast VEGAS acceptor vector that comprises at one end the VA1 sequence and at the other end the VA2 sequence, the linearized yeast VEGAS acceptor vector further comprising a sequence encoding selectable marker functional in bacteria, a selectable marker functional in yeast, a yeast centromere (CEN) sequence, and a yeast autonomously replicating sequences (ARS). The method further comprises iv) introducing into the yeast the linearized yeast VEGAS acceptor vector and the distinct linearized LVA-TU-RVA vector fragments that comprise the distinct TUs. After introduction of these components the method comprises v) allowing homologous recombination in the yeast so that the only one LVA-TU-RVA vector segment comprising the VA1 sequence and the only one LVA-TU-RVA vector segment comprising the VA2 sequence are homologously recombined with the linearized yeast VEGAS acceptor vector to form circularized double stranded DNA polynucleotides comprising at least the two distinct TUs. The method also optionally comprises isolating the circularized double stranded DNA polynucleotides from the yeast. In embodiments, the disclosure includes a plurality of LVA-TU-RVA vectors that comprises at least one, two, three or four additional distinct LVA-TU-RVA that are homologously recombined into a contiguous polynucleotide in yeast.

In embodiments the disclosure comprises yeast cells comprising a homologously recombined DNA molecule made by a process described herein. Compositions comprising homologously recombined DNA molecules isolated from the yeast cells are included, as the isolated recombined DNA molecules themselves. Kits comprising polynucleotides for performing one or more methods of the disclosure are included, and can further comprise reagents for digesting, ligating, isolating, purifying, transforming or transfecting yeast. The kits can further comprise printed material providing instructions for carrying out any embodiment(s) of the disclosure.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 4. VEGAS with PCR-mediated homology to assemble a four gene pathway. (A) TUs flanked by unique VAs are assembled by yGG and then subjected to PCR using primers that introduce terminal homology between adjacent parts. In this example, the reverse primer amplifying TU1 encodes 30 bp of sequence homology to VA4 and the forward primer amplifying TU2 encodes 30 bp of sequence homology to VA3. Together this generates 60 bp of terminal sequence homology between TU1 and TU2 for the homologous recombination machinery in *S. cerevisiae* to assemble a linear piece of DNA in vivo. (B) Gene order may be changed by using different overhang primers; here the final pathway structure becomes TU1-TU3-TU4-TU2, although any order and/or gene orientation is possible and depends only on primer design.

DESCRIPTION OF THE DISCLOSURE

Figure 1:
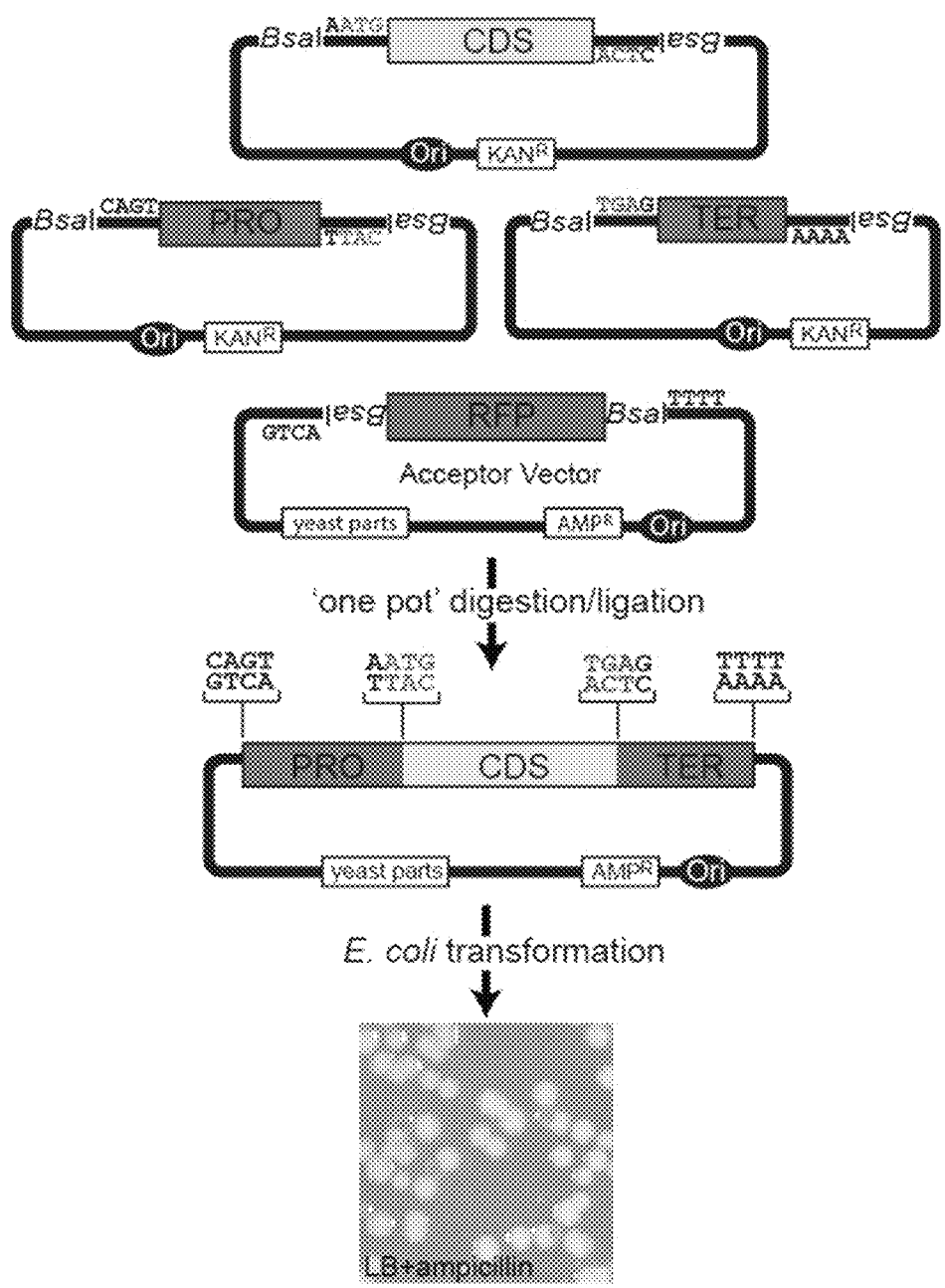
FIG. 1. One-pot yGG assembly. PRO, CDS, and TER parts flanked by the appropriate prefix and suffix sequences are cloned into kanamycin resistant vectors. For 'one-pot' digestion-ligation reaction cloned parts are mixed in equimolar ratio with ampicillin resistant "acceptor vector" for subsequent yGG assembly of TUs. The parental acceptor vector encodes a red fluorescent protein (RFP) gene with *E. coli* promoter and terminator sequences. Following *E. coli* transformation, white/red screening can be used to distinguish clones encoding putative TU assemblies as compared to unmodified parental vector.

The present disclosure is related to improved compositions and methods that are useful for assembling sets of genes for expression in cells. A variety of cell types cells can be modified and used according to embodiments of this disclosure, provided the cells have the ability to promote homologous recombination, whether endogenously or having been engineered to facilitate homologous recombination. In embodiments, the cells are eukaryotic cells. In embodiments, the eukaryotic cells are single-celled organisms. In embodiments, the single-celled eukaryotic organisms are members of the taxonomic kingdom Fungi. In embodiments the organisms are *Ascomycota*. In embodiments, the organisms are the members of *Saccharomyces, Kluyveromyces, Pichia, Candida, Aspergillus, Penicillium, Fusarium, Claviceps, Schizosaccharomyces, Hansenula, Sordaria, Neurospora,* or *Fusarium*. In embodiments, the single-celled eukaryotic organisms comprise yeasts or molds. Non-limiting embodiments of this disclosure are illustrated using *S. cerevisiae*.

In particular, the disclosure encompasses what is referred to as a Versatile Genetic Assembly System (VEGAS), thus providing a new method to construct genetic pathways for expression in eukaryotic cells, such as *S. cerevisiae*. The disclosure includes assembly of a plurality of genes, or transcription units (TUs), using modifications of the so-called Golden Gate approach, and combines a yeast-specific Golden Gate approach referred to herein as yeast Golden Gate (yGG) with homologous recombination performed in yeast, yielding the VEGAS aspect of the disclosure. In the VEGAS aspect, each TU is assigned a pair of VEGAS adapters that assemble up- and downstream of each TU; it is the VEGAS adapter sequences that subsequently provide terminal homology for overlap-directed assembly by homologous recombination 'in yeasto'. As proof of principle, we apply the VEGAS methodology to the assembly of the β-carotene and violacein biosynthetic pathways, whose pigmented products are visible in yeast colonies. Moreover we demonstrate the capacity of VEGAS for combinatorial assembly, thus creating the potential to assemble a wide variety of TUs that can impart to the yeast the capability to perform myriad functions.

This disclosure comprises but is not limited to every polynucleotide sequence described in the accompanying sequence listing, as well as each polynucleotide sequence presented in the text, and those depicted in the Figures. The disclosure includes fragments of each of these polynucleotide sequences, wherein the fragments contain at least 4 contiguous nucleotides of any of the polynucleotide sequences. Each polynucleotide sequence disclosed herein includes its complementary sequence. Thus, every sequence provided in the 5'-3' orientation is considered to include a description of the complementary 3'-5' sequence, and vice versa. For every polynucleotide sequence disclosed herein double stranded and single stranded polynucleotides are included, as are polynucleotides that are only partially double stranded, such as a polynucleotide having a single-stranded overhang that is created by, for example, digestion with a Type IIS restriction enzyme. Single stranded overhangs include those having a 3' or a 5' terminal nucleotide. Kits comprising any one or any combination of the polynucleotides described herein are included in the disclosure. The kits can include any one or any combination of the vectors described herein, primers, restriction enzymes, a ligase, suitable buffers for one-pot restriction digestion and ligase reactions, reagents for introducing linear DNA molecules into yeast, and reagents for separating vectors or other polynucleotides of this disclosure from cell cultures, and/or for purifying such vectors or other polynucleotides. In embodiments the kits comprise reagents for use in assembling a set of genes for heterologous expression in yeast, wherein at least some members of the set of genes encode proteins that cooperate in one or more biosynthetic pathway(s), wherein expression of the proteins is necessary, and may be necessary and sufficient, for the production of a particular product. The product can be any product that can be synthesized by yeast modified according to this disclosure and is not particularly limited. Some non-limiting examples of such products include carotenoids, such as beta-carotene, phyotene, lycopene, and violacein. The disclosure also includes but is not limited to synthesis of classes of pharmacologically active compounds, such as polyketides, non-ribosomal peptides, terpenes, carbohydrates, and derivatives of tryptophan and other amino acids. Thus, the disclosure comprises the synthesis of any substance, molecule, compound or complex that can be made by a cell expressing a plurality of genes via the presently provided approaches.

In one aspect the disclosure generally comprises compositions and methods for making recombinant vectors suitable for homologous recombination with each other in unicellular micyeast, and further comprises facilitating the homologous recombination to produce a polynucleotide comprising a plurality of transcription units. In embodiments, the disclosure includes polynucleotides that comprise a promoter sequence, a coding sequence, and a transcription termination sequence, which collectively comprise a transcription unit (TU). In an embodiment a method of the disclosure comprises: i) providing a first recombinant vector (CDS vector) comprising a protein coding sequence (CDS sequence) wherein the CDS is flanked on its 5' and 3' ends by first Type IIS restriction enzyme recognition sites, the CDS vector further comprising a first antibiotic resistance gene; ii) providing a second recombinant vector (PRO vector) comprising a promoter sequence (PRO sequence) wherein the PRO sequence is flanked on its 5' and 3' ends by the first Type IIS restriction enzyme recognition sites, the PRO vector further comprising the first antibiotic resistance gene; iii) providing a third recombinant vector (TER vector) comprising a transcription termination sequence (TER sequence) wherein the TER sequence is flanked on its 5' and 3' ends by the first restriction Type IIS enzyme recognition sites, the TER vector further comprising the first antibiotic resistance gene; iv) providing a fourth recombinant vector (LVA vector) comprising a first left adapter polynucleotide sequence (LVA sequence) wherein the LVA sequence is flanked on its 5' and 3' ends by the first Type IIS restriction enzyme recognition sites, the LVA vector further comprising the first antibiotic resistance gene; v) providing a fifth recombinant vector (RVA vector) comprising a first right adapter polynucleotide sequence (RVA sequence) wherein the RVA sequence is flanked on its 5' and 3' ends by the first Type IIS restriction enzyme recognition sites, the RVA vector further comprising the first antibiotic resistance gene; vi) providing a sixth recombinant vector (acceptor vector) comprising a segment, the segment comprising a polynucleotide sequence encoding a detectable marker (detectable marker sequence), wherein the detectable marker sequence is flanked by the first Type IIS restriction enzyme recognition sites, and wherein the segment is flanked by a second Type IIS restriction enzyme recognition sites, wherein the acceptor vector comprises a second antibiotic resistance gene but does not comprise the first antibiotic resistance gene; vii) concurrently incubating the CDS vector, the PRO vector, the TER vector, the LVA vector, the RVA vector, and the acceptor vector, such as in a single reaction container, with a first Type IIS restriction endonuclease that recognizes the first Type IIS restriction endonuclease recognition site and a DNA ligase enzyme such that ligated vectors are produced, wherein the ligated vectors comprise sequentially the LVA sequence, the PRO sequence, the CDS sequence, the TER sequence, and the RVA sequence (LVA-TU-RVA vectors), wherein the PRO, CDS and TER sequences comprise a transcription unit (TU), and wherein the LVA-TU-RVA vectors comprise the second antibiotic resistance gene, but do not comprise the first antibiotic resistance gene, wherein the LVA-TU-RVA vectors do not comprise the detectable marker sequence, and wherein the ligated vectors do not comprise the first Type IIS restriction site, but do comprise the second Type IIS restriction site; viii) introducing the LVA-TU-RVA vectors from vii) into bacteria and culturing the bacteria with a culture medium comprising an antibiotic to which bacteria comprising the LVA-TU-RVA vectors are resistant via expression of the second antibiotic resistance gene such that clonal colonies of the bacteria comprising the VEGAS vectors are formed, wherein the clonal colonies do not express the detectable marker; and viii) isolating the LVA-TU-RVA vectors from the colonies that do not express the detectable marker to obtain isolated LVA-TU-RVA vectors. In certain embodiments, the disclosure comprises C-terminally tagged TUs as described further below. In certain embodiments, oligonucleotides can be substituted for vectors or vector parts, or can be used in combination with the vectors of this disclosure, as also described further below.

With respect to the parts of the vectors that are encompassed by this disclosure, the PRO sequence can be any suitable eukaryotic promoter that can facilitate transcription of the CDS sequence in yeast. In this regard, many promoter sequences that can drive transcription in yeast are known in the art. For example, the Promoter Database of *Saccharomyces cerevisiae* (SCPD) includes promoter regions for approximately 6,000 yeast genes, and also includes regulatory elements and transcription factors that can also be taken into account when approaching various aspects of this disclosure if desired. The SPCD can be accessed via rulai.cshl.edu/SCPD/. In embodiments, the promoter is a constitutively active promoter or an inducible promoter. In embodiments the promoter is a strong promoter, a medium promoter, a weak promoter, or a minimal promoter. In embodiments the promoter is not native to the yeast genome, and is inducible by the presence/absence of a small molecule, such as a tet-inducible promoter. Combinations of distinct promoters can be used with different TUs to achieve, for example, a desired stoichiometry of RNA and/or protein products when transcription is driven by the distinct promoters. In embodiments, the PRO drives transcription of RNA Polymerase II.

The CDS can be any sequence that is transcribed into RNA. In embodiments, the CDS encodes a peptide, polypeptide or protein. Those skilled in the art will recognize that any peptide, polypeptide or protein can be encoded by the CDS and, given an appropriate promoter in communication with the CDS, can be expressed in yeast. Thus, the CDS can comprise one or more open reading frames (ORFs). The CDS can encode in certain embodiments, an enzyme, or a structural protein, or a receptor, a ligand for a receptor, a peptide hormone, a binding agent such as an antibody or fragment thereof, a protein that binds one or more compounds such as for storage or transport, a transcription factor or other DNA or RNA binding protein, a contractile protein, or any other type of protein. Alternatively, the CDS can encode an RNA that is not an mRNA. For example, the CDS could encode an RNA that has a regulatory or other function. In embodiments, the CDS encodes an RNA that is capable of participating in RNAi mediated degradation of a target RNA, and can accordingly comprise an siRNA, an shRNA, a microRNA, or a ribozyme. In embodiments, the CDS encodes a Small nucleolar RNA (snoRNAs), a guide RNA or trans-activating crRNA (tracrRNA), such as for use with a CRISPR-based DNA editing system. In embodiments, the RNA encoded by the CDS can comprise a tRNA, an rRNA, or another RNA that can form a component of a Ribonucleoprotein (RNP).

The TER sequence can comprise any suitable transcription termination sequence which functions to designate a location on the transcription template where the RNA polymerase is released from transcription in yeast. In embodiments, the TER sequence can comprise or is immediately juxtaposed to a polyadenylation signal. In embodiments, the TER is followed by TTTT or AAAA. In embodiments, the TTTT or AAAA is present in a single-stranded overhang. Further, a variety of suitable termination signals are known in the art (i.e., Guo Z and Sherman F., 3'-end-forming signals of yeast mRNA. Trends Biochem Sci. 1996 December; 21(12):477-81; and Curran, K. et al., *Short Synthetic Terminators for Improved Heterologous Gene Expression in Yeast*. ACS Synth. Biol. DOI: 10.1021/sb5003357).

The Type IIS restriction enzymes and their recognition sites are all well known in the art. In embodiments, the disclosure includes pairs of Type IIS restriction sites that flank certain segments of vectors as described further below. In embodiments, the Type IIS restriction sites can be inwardly facing with respect to the segment they flank. This configuration is illustrated, for example FIG. 1, in which the top vector includes a pair of inwardly facing BsaI sites that flank the CDS. The sequence AATG sequence shown after the BsaI site illustrates a single stranded overhang that would be left after cleavage using BsaI. It should be recognized that AATG sequence, and the sequence ACTC which is depicted at the other end of the CDS, represent a specific prefix and suffix sequence, respectively. These sequences are comprised within designed sequences that enable directional assembly of TUs via the inwardly facing Type IIS restriction sites with a 4 bp overhang separated from the recognition sequence by a single base to accommodate the offset cutting by the enzyme. These Type IIS sites can be oriented such that they are eliminated upon digestion, and which exposes the designed overhangs. Representative and non-limiting examples of prefix and suffix sequences that are suitable for use with the present disclosure are presented in Table 1, but others can be designed by those skilled in the art given the benefit of the present disclosure. In embodiments, the disclosure also includes use of outwardly facing Type IIS recognition sites. This configuration is illustrated in a non-limiting embodiment in the Acceptor Vector of FIG. 1, wherein the Red Fluorescent Protein (RFP) coding sequence is flanked by outwardly facing BsaI sites.

Figure 6:
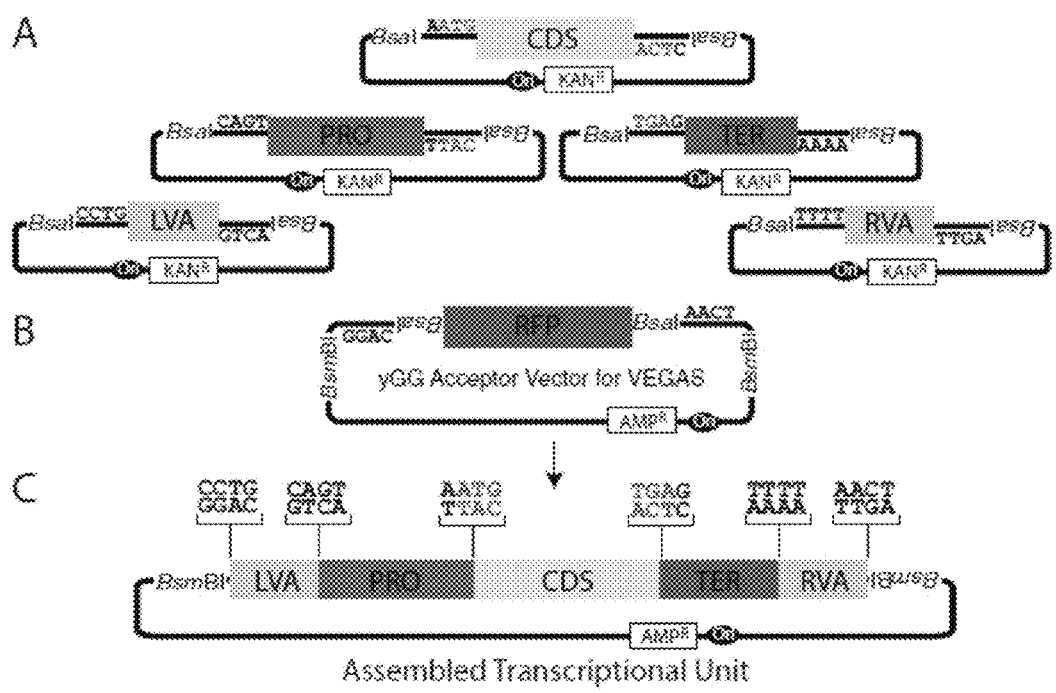
FIG. 6. Yeast Golden Gate (yGG) to assemble transcription units flanked by VEGAS adapters. (A) yGG reactions to build transcription units (TUs) destined for VEGAS pathway assembly in *S. cerevisiae* include 5 parts: a left VEGAS adapter (LVA), a promoter (PRO), a coding sequence (CDS), a terminator (TER), and a right VEGAS adapter (RVA). Each part is flanked by inwardly facing recognition sequences for the BsaI restriction enzyme, an "offset cutter" which cuts outside its recognition sequence (at positions 1/5 bp downstream) to expose the indicated 4 base-pair overhangs. All parts are cloned into vectors encoding kanamycin resistance ($KAN^R$) and an *E. coli* replication origin (Ori). (B) The yGG acceptor vector for VEGAS is designed such that outwardly facing BsaI sites expose overhangs corresponding to the 5' LVA and 3' RVA overhangs to promote assembly of the TU in the vector during a one-pot restriction-digestion reaction. The RFP cassette, built for expression in *E. coli*, is cut out of the vector when a TU correctly assembles, enabling white-red screening. The yGG acceptor vector encodes resistance to ampicillin ($AMP^R$) (C) The structure of a VA-flanked TU assembled by yGG. An assembled TU plus the flanking VA sequences may be released from the yGG acceptor vector by digestion with BsmBI.

In embodiments, the disclosure includes using a second Type IIS restriction enzyme and its recognition sequence. For example, in a non-limiting embodiment, FIG. 6 depicts a VEGAS acceptor vector that comprises an RFP segment flanked by outwardly facing BsaI sites, and that segment is itself flanked by inwardly facing BsmBI sites. It should be recognized that reference to "first" and "second" Type IIS restriction enzymes and sites is for convenience and does not necessarily specify order or preference. The same applies to the terms "first" and "second" etc. as used to describe other parts of embodiments of this disclosure. It is considered that any other Type IIS restriction endonucleases and their concomitant recognition sequences can be adapted for use in methods of this disclosure. For example, in embodiments, a combination of different Type IIS restriction enzymes and sites can be used in assembling a TU as described herein, so long as they can all function in the same reaction, and provided that the combination of sites used in the CDS, PRO and TER vectors, for example, are not also encoded on the acceptor vector illustrated in Panel C of FIG. 6.

In embodiments, certain vectors and linearized polynucleotides encode antibiotic resistance genes. A wide variety of antibody resistance genes are known in the art and can be used with embodiments of this disclosure. In one approach, two distinct antibiotic resistance genes are used. In one embodiment, a first antibiotic resistance gene comprises a kanamycin resistance gene. In an embodiment, a second antibiotic resistance gene comprises an ampicillin resistance gene.

Figure 2:
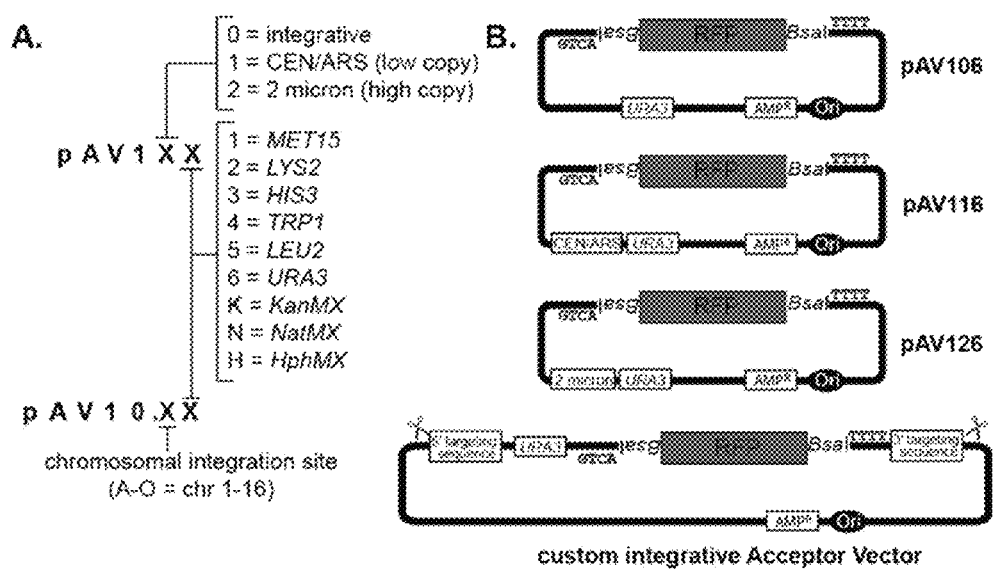
FIG. 2. yGG acceptor vectors. (A) Schematic representation of acceptor vector nomenclature. (B) Schematic of representative acceptor vectors. All yGG acceptor vectors (AVs) encode resistance to ampicillin ($AMP^R$) or chloramphenicol (not pictured) to permit construction of TUs in a 'one-pot' reaction with PRO, CDS, and TER parts that are cloned into kanamycin resistant vectors. Following transformation of yGG reaction products into *E. coli*, white/red screening can be used to identify clones encoding assembled constructs.

In embodiments, the vectors of this disclosure comprise shuttle vectors, and thus they comprise components that permit their propagation in prokaryotic and eukaryotic cells. In embodiments, the vectors comprise one or any combination of a prokaryotic origin of replication (Ori), an auxotrophic marker functional in yeast (i.e., URA3 or any of a wide variety of the other suitable autotrophic marker genes), and a sequence facilitating episomal replication in yeast, such as a centromere/autonomously replicating sequence (CEN/ARS). Suitable CEN and ARS sequences are well known in the art. Thus, in embodiments, the disclosure comprises a plurality of distinct TUs in a vector that is maintained episomally in yeast, and yeast comprising such episomal elements. In certain embodiments, the disclosure includes vectors that are adapted for integration into a yeast chromosome, and thus do not comprise CEN/ARS sequences. Representative and non-limiting examples of such acceptor vectors designed for integration into the URA3, LEU2, TRP1, and HIS3 loci are shown in FIG. 2. The disclosure thus encompasses integration of a plurality of TUs into a yeast chromosome, and yeast comprising such integrations. The disclosure accordingly includes integrative acceptor vectors (FIG. 2) that comprise a polynucleotide sequence that is homologous to an innocuous site in the yeast genome. Non-limiting examples of such sites include the HO locus on chromosome 4, intergenic regions on the left arm of chromosome 6 and right arm of chromosome 9, and a dubious ORF on chromosome 11 (YKL162C-A) (see Table 2).

In one embodiment a vector used in the disclosure encodes a detectable marker. In general, the marker can be (but does not necessarily need to be) a visually detectable marker, such as a protein that participates in the production of a color that is visually perceptible by a human. In this regard, red fluorescent protein (RFP) is used to facilitate selection of bacteria that contain properly assembled vectors, and as such they do not express RFP due to excision of its coding sequence from the properly assembled constructs. However, a detectable marker could also be configured to identify properly assembled constructs via its expression. Thus, there are a variety of detectable markers and configurations of them that can be implemented in various approaches to facilitate isolation of properly assembled constructs, and these alternative approaches will be apparent to those skilled in the art given the benefit of the present disclosure.

In embodiments, vectors of this disclosure comprise VEGAS adapter sequences. The VEGAS adapter sequences are referred to as "left" and "right" simply to illustrate their position relative to the sequential PRO, CDS, TER orientation of the vectors as will be readily apparent from the Figures of this description. The left and right VEGAS adapters are from time to time referred to as LVA and RVA, respectively, in this disclosure. The VEGAS adapter sequences are orthogonal to the yeast genome, and thus, in certain embodiments, a VEGAS sequence is not part of the genome of yeast into which a vector comprising the VEGAS adapter sequence is introduced. This is intended to preclude inadvertent recombination with the yeast chromosome, but it will be recognized that the disclosure does not exclude intentionally designed recombination with a yeast chromosome as described further below. The VEGAS adapters participate in combinatorial and sequence oriented recombination of linearized vectors as illustrated generally in FIG. 8. The VEGAS adapters of this disclosure comprise or consist of 35-500 base pairs (bp), inclusive, and including all integers there between and all ranges of integers there between, with the proviso that the adapters are: a) less than 90% identical to any contiguous sequence in the genome of the cell type into which they are introduced, such as a yeast, wherein the less than 90% range includes all integers including and between 90% and 0% identity, including all ranges of integers there between, and in certain embodiments are less than 50% identical to the genome of the receiving cell; b) orthogonal to each other, meaning the LVA and RVA on the same vector are less than 90% identical to each other, wherein the less than 90% range includes all integers including and between 90% and 0% identity, including all ranges of integers there between, and in certain embodiments are less than 50% identical to the each other, wherein the identity is applied either between VA pairs, or for all VAs used in any particular situation, and c) comprise greater than 30% GC content and less than 70% GC continent in base composition; thus, the VAs in certain embodiments comprise from 30% to 70% GC content, inclusive, and including all digits and ranges of digits there between. The disclosure includes representative and non-limiting VEGAS adapter sequences that are presented in Table 3. In embodiments, a vector comprising an LVA, a TU and an RVA is referred to herein as an "LVA-TU-RVA" vector.

In embodiments, the disclosure provides vectors which comprise parts selected from: a CDS sequence that comprises on its 5' end the sequence: AATG and at its 3' end the sequence TGAG; a PRO sequence that comprises at its 5' end the sequence: CAGT and at its 3' end the sequence AATG; a TER sequence that comprises at its 5' end the sequence TGAG and at its 3' end the sequence TTTT; an LVA sequence that comprises at its 5' end the sequence CCTG and at its 3' end the sequence CAGT; an RVA sequence that comprises at its 5' end TTTT and at its 3' end the sequence AACT; and in certain cases, a detectable marker sequence that comprises at its 5' end the sequence CCTG and at its 3' end the sequence AACT. In certain embodiments, the disclosure includes a first LVA sequence that comprises or consists of the sequence:

```
(VA1*)
                                          (SEQ ID NO: 1)
CCCCTTAGGTTGCAAATGCTCCGTCGACGGGATCTGTCCTTCTCTGCC
GGCGATCGT.
```

In certain embodiments, the disclosure includes a first RVA sequence that comprises or consists of the sequence:

```
(VA2**)
                                          (SEQ ID NO: 2)
TGACGCTTGGATGCGTGACCCCGTACGTCATGACCCGTCATGGGTATG
TAAGCGAAG.
```

Figure 8:
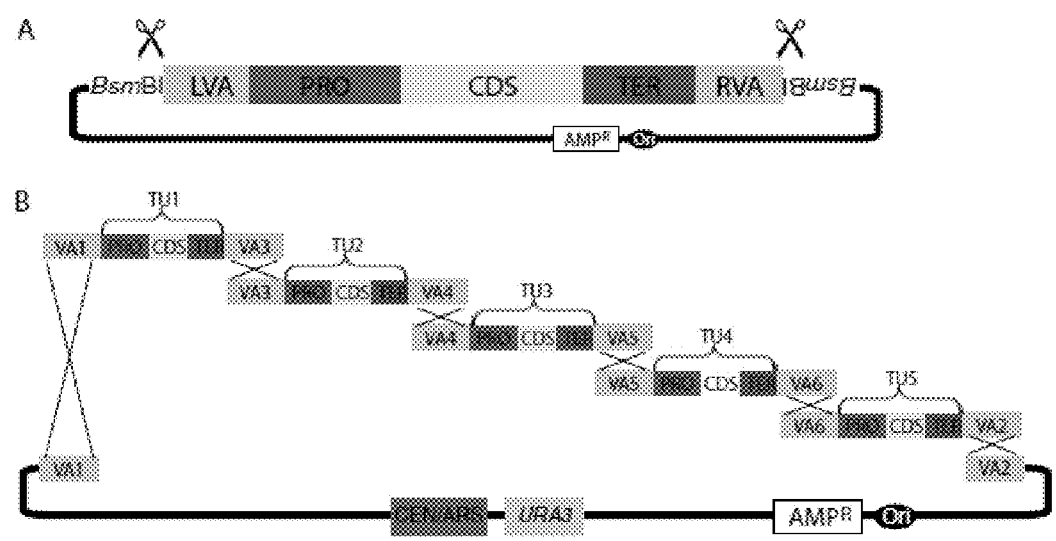
FIG. 8. VEGAS with adapter homology to assemble a five gene pathway. (A) The pathway consisting of VA-flanked TUs assembled by yGG may be released in one piece from the yGG acceptor vector by digestion with BsmBI (scissors). (B) A genetic pathway may be assembled into the linearized VEGAS assembly vector in *S. cerevisiae* by homologous recombination between VAs that flank TUs (TU1-5). X's indicate homologous recombination.

In an aspect the disclosure includes producing a homologously recombined DNA molecule comprising distinct TUs described above. The method in one embodiment comprises providing a plurality of LVA-TU-RVA vectors, wherein each LVA-TU-RVA vector in the plurality comprises a distinct TU that comprises a CDS, and wherein each LVA-TU-RVA vector further comprises an LVA sequence and an RVA sequence, wherein only one LVA-TU-RVA vector in the plurality comprises the first LVA sequence (referred to as a "VA1 sequence") that is identical to a first LVA sequence in a yeast VEGAS acceptor vector, and wherein only one LVA-TU-RVA vector in the plurality comprises a first RVA sequence (referred to as a "VA2 sequence") that is identical to a first RVA sequence in a yeast VEGAS acceptor vector. The plurality of the LVA-TU-RVA vectors is linearized by digestion with a Type IIS restriction enzyme that recognizes a Type IIS restriction site, thus yielding distinct linearized LVA-TU-RVA vector fragments that comprise the distinct TUs. The method further comprises providing a linearized yeast VEGAS acceptor vector that comprises at one end the VA1 sequence and at the other end the VA2 sequence, the linearized yeast VEGAS acceptor vector further comprising a sequence encoding selectable marker functional in bacteria, a selectable marker functional in yeast, a yeast CEN sequence, and an ARS sequence. The method comprises introducing into the yeast the linearized yeast VEGAS acceptor vector and the distinct linearized LVA-TU-RVA vector fragments that comprise the distinct TUs, and allowing homologous recombination in the yeast so that the only one LVA-TU-RVA vector segment comprising the VA1 sequence and the only one LVA-TU-RVA vector segment comprising the VA2 sequence are homologously recombined with the linearized yeast VEGAS acceptor vector to form circularized double stranded DNA polynucleotides comprising at least the two distinct TUs. Optionally, the method further comprises isolating the circularized double stranded DNA polynucleotides from the yeast. In certain embodiments, this approach provides a single polynucleotide that comprises two, three, four, five, or six, or more, TUs. Certain steps of this approach are illustrated in FIG. 8, which also illustrates an approach to configuring the LVA and RVA sequences such that they are recombined in the yeast in a predetermined order that is dictated at least in part by the homology of the distinct LVA and RVA sequences. In particular, as will be evident from FIG. 8, the disclosure includes providing an RVA sequence on one linearized vector that is the same as an LVA sequence on a distinct linearized vector to enable the yeast to homologously recombine the two vectors into a contiguous polynucleotide. The approach can be repeated iteratively using different LVA and RVA sequences on distinct linearized vectors to assemble intentionally ordered TUs, as illustrated in FIG. 8.

EXAMPLE 1

This Example provides an illustration of the construction of TUs for expression in *S. cerevisiae* using a yeast Golden Gate (yGG) approach that is modified in Example 2 to include the VEGAS adapter-based approach.

As described above, a TU used in this disclosure contains three parts: a UAS/promoter/5'UTR (PRO), a coding sequence (CDS), and a 3'UTR/polyadenylation signal/terminator (TER). To enable directional assembly of TUs we assign specific prefix and suffix sequences to each of the three parts that encode "inwardly facing" Type IIS restriction sites, typically BsaI or BsmBI, and a 4 bp "designer overhang" separated from the recognition sequence by a single base to accommodate the offset cutting by the enzyme (Table 1). These Type IIS RE sites are oriented such that they are eliminated upon digestion, exposing designer overhangs as follows: 5'-CAGT-PRO-AATG-3',5'-AATG-CDS-TGAG-3', and 5'-TGAG-TER-TTTT-3', respectively (FIG. 1). (Note that all overhangs are listed here as top strand sequences for clarity, but are the bottom strands are given in certain instances in the Figures.) The overhangs selected are known to be highly compatible with regulated gene expression and represent the smallest possible scars as they exploit the natural punctuation marks ATG and TGA. Specifically, the AATG overhang between the PRO and CDS provides the ATG start codon. This overhang provides a favorable context for gene expression, as most well-expressed yeast genes have their ATG initiation codons preceded by one or more A's. Additionally, the TGAG overhang at the CDS/TER junction provides a universal TGA stop codon. PRO, CDS, and TER parts flanked by the appropriate prefix and suffix sequences are cloned into, for example, kanamycin resistant vectors that do not encode genetic information for replication in yeast. The subsequent yGG assembly of TUs is performed using, for example, an ampicillin resistant "acceptor vector" in a 'one-pot' digestion-ligation reaction as described further below. The parental acceptor vector encodes detectable marker, such as a red fluorescent protein (RFP) gene with E. coli promoter and terminator sequences. Thus, in this embodiment, following E. coli transformation, white/red colony color screening can be used to distinguish clones encoding putative TU assemblies from those containing unmodified parental vector.

Acceptor Vectors.

We have constructed a series of illustrative acceptor vectors with multiple markers and applications for use in vector assembly (Table 2). To facilitate TU assembly, acceptor vectors lack, for example, BsaI and/or BsmBI restriction sites except for two outwardly facing sites flanking the RFP cassette described above. The overhangs generated following BsaI (or BsmBI) digestion are compatible with receiving the 5' overhang of the PRO part (CAGT) and the 3' overhang of the TER part (TTTT). Subsequent to assembly, these vectors permit direct transformation of TUs into yeast cells.

The first two sets of yGG acceptor vectors are intended for independent replication and segregation once transformed into S. cerevisiae and derive from the well-known pRS series of yeast shuttle vectors pRS41X and pRS42X. These vectors encode either a centromere/autonomously replicating sequence (CEN/ARS) combination (pRS41X; single copy) or 2 micron parts (pRS42X; high copy), in addition to a selectable marker for yeast, plus selection and replication parts for bacteria (ampicillin resistance and a replication origin; FIG. 2).

The third type of acceptor vector is intended for integration into a specific locus in the yeast genome and therefore lacks genetic parts that enable independent replication in yeast (e.g. CEN/ARS or 2 micron sequences). To this end, as with the other two sets of pRS vectors we have converted the pRS40X series into yGG TU acceptor vectors for integration into the URA3, LEU2, TRP1, and HIS3 loci (FIG. 2). Furthermore, we have designed and built a series of custom integrative acceptor vectors (FIG. 2). Here, a yeast selectable marker is encoded on one side of the BsaI-RFP-BsaI cassette, and together these parts are flanked by ~500 bp regions targeting an innocuous site in the yeast genome. These sites include the HO locus on chromosome 4, intergenic regions on the left arm of chromosome 6 and right arm of chromosome 9, and a dubious ORF on chromosome 11 (YKL162C-A) (Table 2). To facilitate integration, on either side of the targeting sequences each custom integrating acceptor vector encodes rare cutting restriction sites such as BciVI and/or NotI (Table 2). Digestion with the second enzyme can excise the entire integration cassette, generating a substrate for recombination with the corresponding endogenous locus in the yeast chromosome.

Designing and Constructing PRO, CDS, and TER Parts.

The boundaries of PRO, CDS, and TER parts are determined using rules that enable the automated extraction of their sequences from the yeast genome (or elsewhere). Because the start and stop codon of a CDS are encoded by the designer overhangs as part of prefix and suffix sequences, in certain embodiments a CDS part is defined to extend from the second codon of the open reading frame of a gene through the last "sense" codon. For PRO and TER parts extracted from the S. cerevisiae genome, the disclosure includes boundary definition rules based on commonly accepted, average sequence length for these two types of genetic elements. Specifically, in certain embodiments, yeast PRO segments are defined as the DNA extending 5' of the ATG codon of the gene of interest for either (i) 500 bp or (ii) the nearest upstream gene boundary, whichever is shorter. TER sequences in certain embodiments are defined as the sequence 3' of the CDS that extend either (i) 200 bp or (ii) the nearest downstream gene boundary, whichever is shorter.

Prefix and suffix sequences can be appended to parts in at least three ways: (i) The appropriate overhang can be encoded by primers such that the resulting PCR product encodes the appropriate sequences; this is typically done for PRO and TER sequences cloned out of S. cerevisiae. (ii) The prefix and suffix can be built into the design of parts to be made by polymerase chain assembly or other means of DNA synthesis; this is typically done for CDSs derived from other organisms as we first re-code the CDS to optimize codon usage for expression in S. cerevisiae using commercially available software (iii) The prefix and suffix could be ligated to a pre-existing part as adapter or linker sequences.

Figure 5:
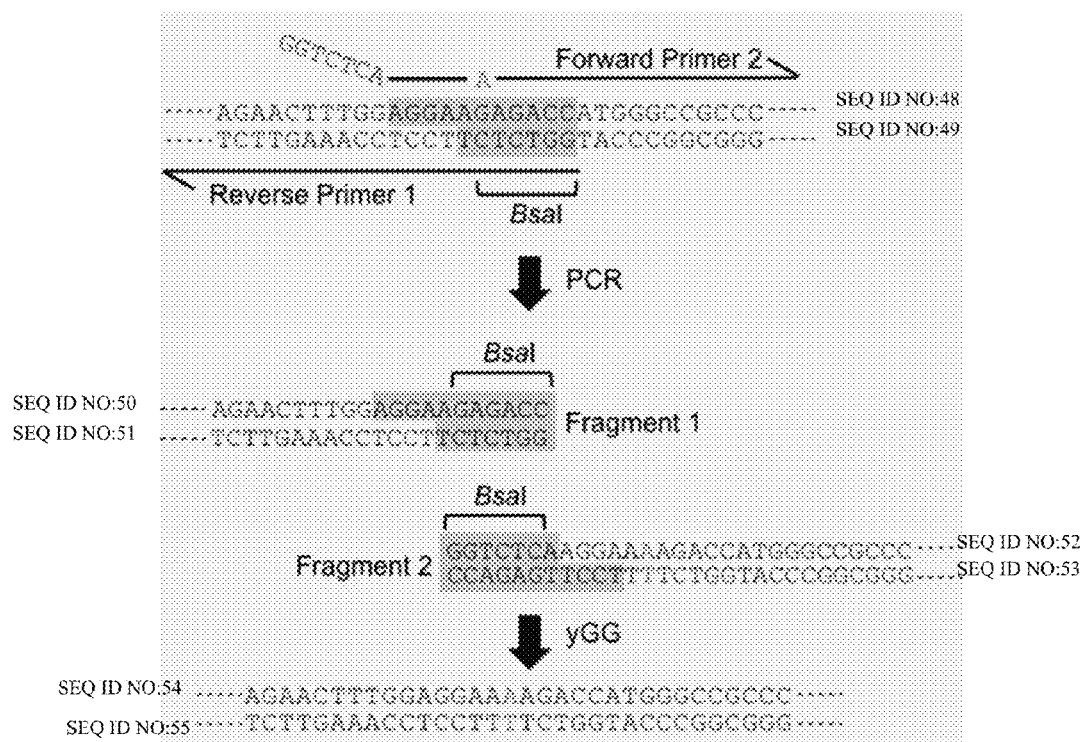
FIG. 5. Elimination of a BsaI site using yGG. Schematic representation of the design of parts in order to eliminate a BsaI restriction site to enable one-pot assembly using yGG. For a BsaI site oriented to cut upstream of its recognition site, two primers should overlap the site; one reverse primer (Reverse primer 1) that will amplify the sequence upstream (Fragment 1) and will include the recognition site. The second primer (Forward Primer 2) will amplify the sequence downstream (Fragment 2), mutate the original restriction site (mutated site marked in red) oriented to create a complementary overhang to the upstream fragment. Following yGG the product will have no BsaI recognition site.

In cases where a forbidden site exists internally to a part there are multiple ways to eliminate the site. Most directly, after subcloning, the forbidden site can be changed using site directed mutagenesis. Alternatively, one can design a modified version of the part to be synthesized. The forbidden type IIS restriction site can be eliminated by constructing a pair of sub-parts that can be used together in yGG reactions (illustrated in a non-limiting embodiment in FIG. 5). In general it is considered that changing one base in a PRO or TER part is unlikely to alter the function of the part, and re-coding forbidden sites internal to CDS parts can also be carried out using commercially available software.

In lieu of changing forbidden sites within part sequences, the yGG reaction conditions can also be modified to skip the five minute incubation at 50° C., the second to last step. Eliminating the type IIS restriction digest in this step increases the background of intact parental vector, but leaves some proportion of correct assemblies with ligated internal sites. Although one would expect both a lower yield of correct assemblies as well a higher background of intact parental vector to transform E. coli, the detectable selection marker, i.e., the white/red selection system built into our yGG workflow makes it easy to distinguish clones with assembled constructs.

Efficiency of yGG Assembly.

Figure 3:
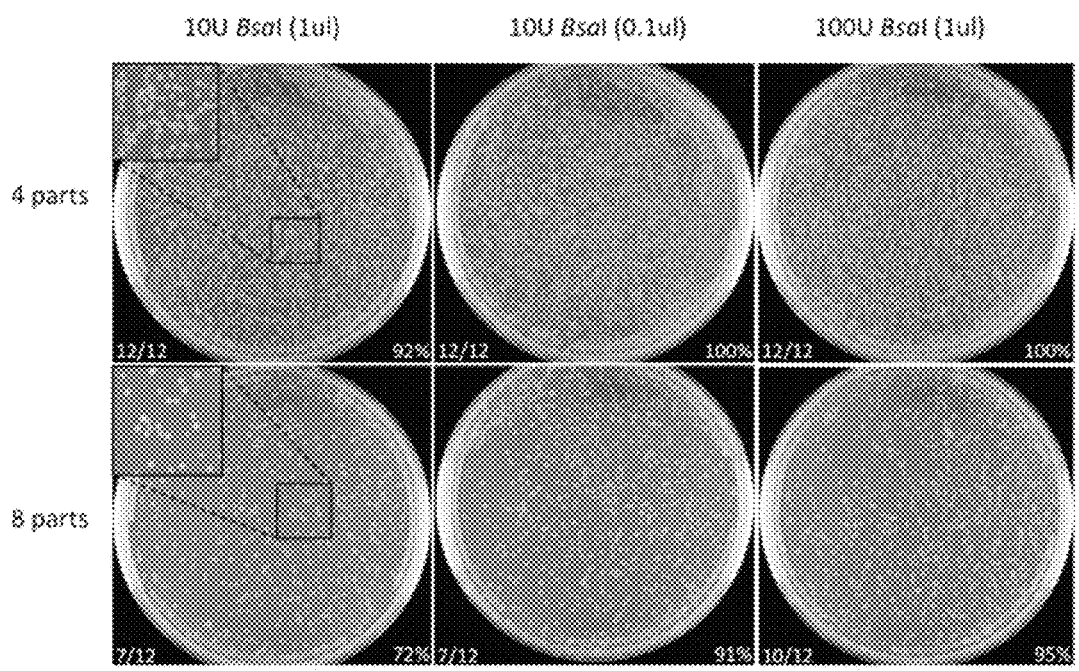
FIG. 3. Efficiency of yGG with different numbers of Parts. 4 part and 8 part yGG assembly was performed in the presence of 10 U, 10 U and 100 U of BsaI with a volume of 1 μl, 0.1 μl and 1 μl of enzyme respectively. The yGG reaction products were transformed into bacteria and plated on LB-Carb plates. Pictures were taken after 1 day's incubation at 37° C. White and red colonies were counted; white colonies percentage is indicated on the lower right of the picture. The fraction on the left hand side is the amount of correct assembly clones, as measured by plasmid prep and digest of 12 white colonies.

The general yGG reaction includes four parts for assembly: a PRO, CDS, TER, and an acceptor vector. In some cases, however, the number of parts can increase, for example if a single CDS is composed of multiple sub-parts or when generating a TU with a C-terminal fusion tag (see below). To examine how the number of parts affects assembly efficiency we compared four- and eight-part yGG reactions using white/red screening as the output, as described further below. Initially we followed an established protocol which specified stock BsaI at 10 U/µL. Here, for the four-part assembly 92% of recovered colonies were white and for the eight-part assembly 72% of colonies were white (FIG. 3). The observation of red transformants suggested to us that the final yGG reaction product contained undigested, parental acceptor vector encoding the RFP cassette. We hypothesized that an insufficient active BsaI might underlie this result. To test this, we obtained a concentrated stock of BsaI (100 U/µL) from New England Biolabs to circumvent the problem that addition of extra BsaI at the standard concentration (10 U/µL) yielded a prohibitive glycerol concentration in the final reaction mixture. Using 100 U of BsaI per reaction (1 uL of 100 U/µL), we recovered 95% white colonies in the eight-part assembly reaction. Moreover, we discovered this result could be re-capitulated for the eight-part assembly (91% white colonies) using only 10 U of the 100 U/µL BsaI stock (0.1 µL). This result indicates that reduced glycerol concentration underlies the improved BsaI digestion efficiency in yGG reactions. Thus, in embodiments, the disclosure comprises using enzymes having the U/μL and glycerol concentrations described herein.

To test whether white-colored transformants encoded correctly assembled TU constructs, we picked 12 colonies from each reaction condition, prepped the plasmids and digested with an appropriate restriction enzyme to test the assembly structure. For the four-part assembly, in each of the three experimental conditions 100% of the selected white colonies yielded the expected digestion pattern. However, in the eight-part assembly the 10 U, 100 U, and 10 U-low glycerol reactions yielded only 7/12, 10/12 and 7/12 correct assemblies, respectively. Four independent incorrect digestion patterns were observed and a single clone representing each class was sequenced to investigate the cause of each misassembly. In two cases an internal CDS overhang (TGGT or GTTG) misassembled with a designer overhang in which 2 base pairs were mismatched to a designer overhang (CAGT or TTTT). The third misassembly occurred between an internal CDS overhang (ACGG) with 3 base pair mismatches to the designer overhang (CAGT). In the final misassembled clone we analyzed the sequencing reaction failed, possibly due to a large deletion or a plasmid contamination. Thus, it is considered that the overhangs internal to the CDS part assembly should be evaluated on a case by case basis, which can be done by one skilled in the art given the benefit of this disclosure.

Based on the foregoing, and without intending to be constrained by any particular theory, it is considered that the yGG process (and the VEGAS adapter approach described below) may be most efficiently performed using 10 U of highly concentrated restriction enzyme to minimize the concentration of glycerol in the reaction. This may be particularly important when assembling TUs with more than four parts. Moreover, our results suggest that the faithful assembly of parts in yGG reactions should include the use of maximally different overhang sequences when possible.

C-Terminally Tagging TUs Generated by yGG.

Figure 4:
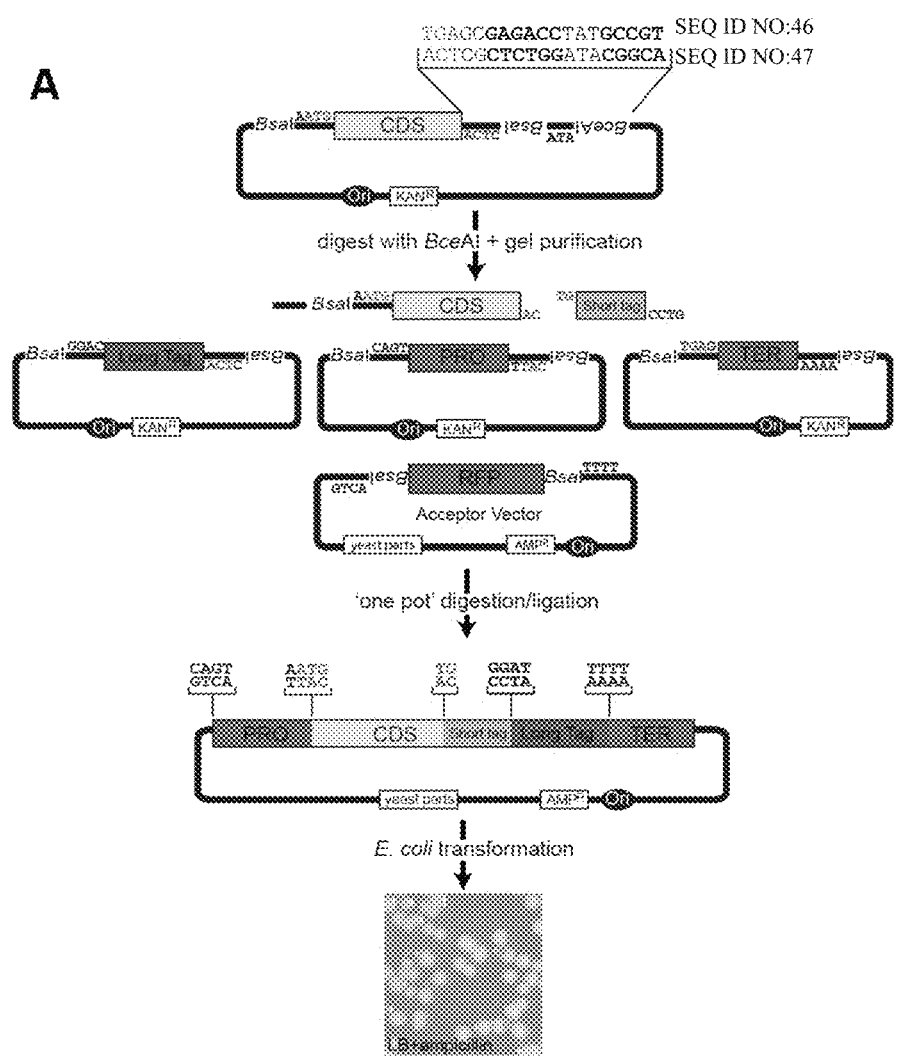
FIG. 4. yGG to construct a TU encoding a C-terminally tagged CDS. (A) The CDS is part flanked by the appropriate prefix and suffix sequences and cloned into a kanamycin resistant vector (Supplementary Data). Prior to TU assembly by yGG, the CDS construct is digested with BceAI and subsequently gel purified. The BceAI digested CDS fragment is mixed with PRO, TER, Long Tag (e.g. GFP, mCherry, TAP, GST) constructs, each flanked by the appropriate prefix and suffix sequences, plus Short Tag (e.g. flag, V5, HA etc.) or linker annealed oligos and desired yGG acceptor vector. The mixture is then subjected to a 'one-pot' digestion-ligation reaction with the appropriate enzymes to assemble the tagged TU. Following *E. coli* transformation, white/red screening can be used to distinguish clones encoding putative TU assemblies as compared to unmodified parental vector. (B) Colony PCR was performed on 13 white colonies from yGG assembly carried out as described in (A). Primers amplified a region around the C-terminus of the V5-GFP tagged protein to differentiate tagged and untagged clones. 10 of 13 amplicons are consistent with the predicted size for the tagged construct. C=untagged construct, M=DNA ladder. (C) Functional validation of C-terminally tagged HTP1. HTP1 C-terminally tagged with GFP or mCherry is functional, thus cells grow on medium containing hypoxanthine as the sole purine source. HPRT, the human ortholog of HPT1 and known to functionally complement is a positive control. Fluorescence microscopy reveals expression of both mCherry and GFP in these cells.
Figure 4:
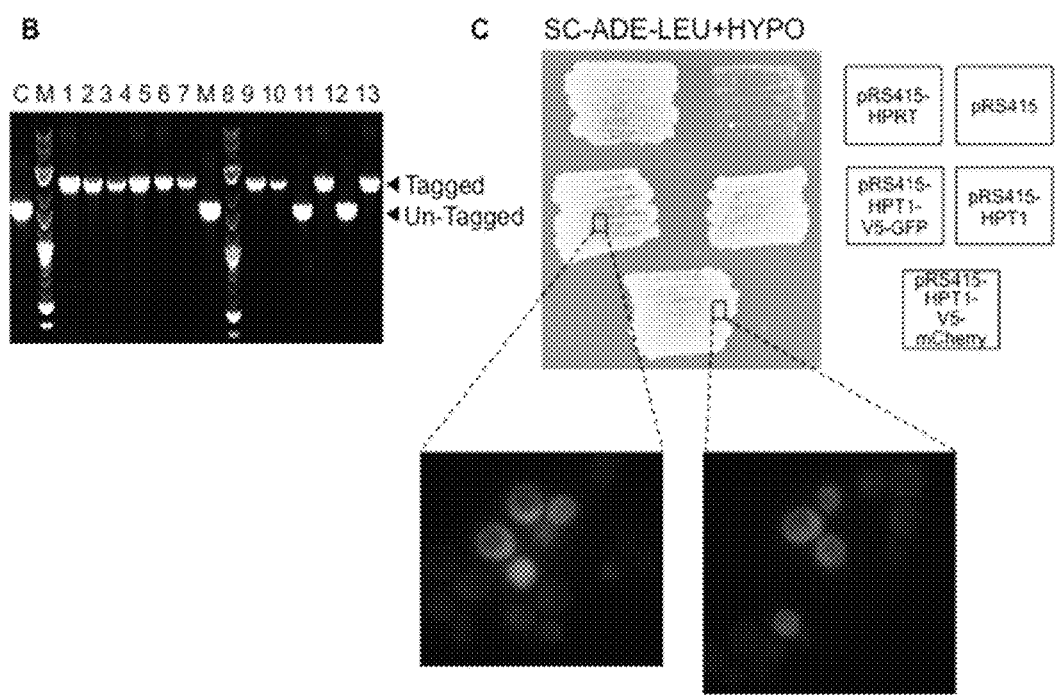

It is often useful to express a tagged version of a protein for fluorescence microscopy, immunopurification, expression level analysis, etc. To this end we have devised a yGG-compatible strategy to generate TUs encoding C-terminal fusion tags, and thus such TUs, methods of making them and methods of using them are encompassed by this disclosure. In these embodiments we assign a special suffix to the CDS part that permits its assembly into a TU in either the untagged or tagged format. Our design utilizes the enzyme BceAI in combination with either BsaI or BsmBI (FIG. 4). BceAI is a 'long reach' type IIS restriction enzyme that cuts 12 and 14 bp from the recognition leaving a 2 base overhang. Although the BceAI recognition sequence is 5 bp in length, it contains the very rarely encountered CpG dinucleotide and is thus underrepresented in the yeast genome relative to other sequences of this length. By embedding a BsaI (or BsmBI) site inside the BceAI site (ACGGCATAGGTCTCGCTCA (SEQ ID NO:3), it is possible to generate one of two different overhangs; BsaI (or BsmBI) digestion in a standard yGG reaction generates a standard 3' CDS overhang of TGAG while BceAI digestion leaves a 2 base overhang consisting of only the "AC" of the complementary strand to the TGA stop codon, allowing read-through to occur. Due to the moderately unreliable digestion pattern of 'long reach' restriction enzymes like BceAI, and to ensure assembly with the digested fragments, we use annealed oligonucleotides in combination with a standard acceptor vector. Those oligos can contain either a short tag (e.g. flag, V5, HA, etc.), or a linker to ensure the C-terminus of the CDS is in frame with sequences of longer tags (e.g. GFP, mCherry, TAP, GST). Longer tags can be provided as yGG-compatible subcloned constructs to which we assign the 3' overhang sequence GGAT. In contrast to the untagged yGG, which may be performed as a 'one-pot' reaction, a tagging yGG reaction requires pre-digestion of the CDS construct with BceAI and gel purification prior to the yGG reaction. The disclosure includes each embodiment described in this approach to tagging TUs.

To test the efficiency of C-terminal tagging by yGG, we built a CDS construct with the appropriate sequences flanking HTP1, whose protein product functions in the purine salvage pathway. The HTP1 CDS part was assembled into a TU by yGG with its native promoter and terminator, along with a V5 tag plus a fluorescent protein tag (either mCherry or GFP). The V5 sequence was provided as annealed oligos and served as a linker to put the fluorescent protein sequence in frame. Assembly efficiency, assessed by PCR with primers spanning the GFP tag, revealed that 10 out of 13 white colonies produced amplicons consistent with correct assembly. Similar results were obtained with the mCherry tag (data not shown). One of each GFP or mCherry tagged HTP1 TU constructs was then subjected to two functional assays. To determine whether HTP1 was expressed we transformed the constructs into a yeast strain in which ADE4 and HTP1 had been deleted from their native genomic loci. In the absence of HTP1 expression, this strain cannot grow on medium containing hypoxanthine as the sole purine source, however, both the mCherry and GFP tagged HTP1 TUs fully complemented the growth on this medium (FIG. 4B). Expression of both mCherry and GFP was also confirmed by fluorescence microscopy (FIG. 4C).

Together this Example demonstrates successful construction of C-terminally tagged TUs by yGG. The reduced efficiency of assembly here as compared to the untagged assembly likely lies in the digestion and gel purification step. Specifically, any undigested CDS carried through the gel extraction step can lead to untagged TU assembly during the yGG reaction. Additionally, long reach IIS enzymes typically cut with less precision than short reach IIS enzymes like BsaI and BsmBI as the sequence composition between the recognition and cut sites can impact DNA movement and stretching.

One of the advantages of the yGG method described herein is the use of the bacterial RFP to select against unmodified parental acceptor vector. However, in some cases there is an obvious selection in yeast that can differentiate between correct and incorrect clones, such as with assembly of an essential yeast transcription unit. In this case, we can bypass the bacterial step and transform the yGG product straight into the yeast cells, and aspects of this approach are demonstrated in Example 2. A modification that could be made to the yGG acceptor vector in this case is to express a yeast marker between the BsaI sites.

Although we propose using yGG to assemble yeast transcription units for expression in yeast, there are other useful applications for this method and for the VEGAS adapter approach described in Example 2. For example, we have used the PRO and TER sequences to serve as homologous sequences for targeted deletion of a specific yeast gene. Using yGG, a selectable marker gene (URA3, KanMX etc.) can be assembled between the PRO and TER of the gene to be deleted. For this, we built a specific acceptor vector (pAV10) without a yeast selectable marker and lacking a yeast replication origin. Additionally, we included rare restriction enzyme (NotI and FseI) recognition sites flanking the TU assembly site. Thus, following assembly using yGG, the fragment containing the PRO, marker and TER can be digested and transformed into yeast for targeted deletion of the gene of interest.

yGG can also be used for expression of non-native genes in yeast by assembling a heterologous CDS with a yeast promoter and terminator. To enable optimal expression in yeast, the gene sequence should be first codon optimized for *S. cerevisiae*, keeping in mind the "forbidden" sites to ensure efficient assembly.

In addition, the concepts of yGG can easily be adapted to mammalian or plant cells. Expression in mammalian cells may require larger more complex promoters but the same yGG concepts can be used once these are defined. Similarly, there is strong evidence that encoding an intron in mammalian expression constructs has a positive influence on expression. An intron could be contained within the PRO segment, or a separate intron segment could be interposed between the PRO and CDS segments or between multiple CDS parts, allowing the evaluation of large numbers of different introns on gene expression, for example.

Thus, use of the assembly strategy in yGG can be expanded for easy cloning in a variety of uses and organisms.

EXAMPLE 2

This Example provides a significant improvement of the yGG described in the Example above, but it should be recognized that features of the above described approach can be included in this Example.

yGG to Assemble TUs Destined for VEGAS.

The yGG method described in Example 1 defines genes as 'transcription units' (TUs) comprising three functionally distinct types of parts: promoters (PRO; these parts subsume UAS, promoter and 5' UTR sequences as a single part), coding sequences (CDS), and terminators (TER; consisting of 3' UTR and polyadenylation signals). In brief, yGG exploits type IIS restriction enzymes that cut outside of their recognition sequences exposing designer, 'biologically meaningful' overhangs to promote assembly of functional TUs (PRO-CDS-TER) in specially constructed acceptor vectors. A distinction made for TUs destined for VEGAS pathway assembly is the addition of two additional VEGAS adapter (VA) parts into the assembly. Here, one VA is designed to assemble upstream of the promoter (LVA, for left VEGAS adapter) and the other for assembly downstream of the terminator (RVA, for right VEGAS adapter). The yGG reaction with VA parts thus generates the following structure: (vector end)-LVA-PRO-CDS-TER-RVA-(other vector end) (FIG. 6). The RVA and LVA designer overhangs and acceptor vector built specifically for assembling VA-flanked TUs are described below. This aspect of the disclosure can also be carried out in a 'one-pot reaction', is compatible with combinatorial assembly (i.e. pools of promoters and terminators in a single reaction), and is amenable to automation.

Designer Overhangs.

Figure 11:
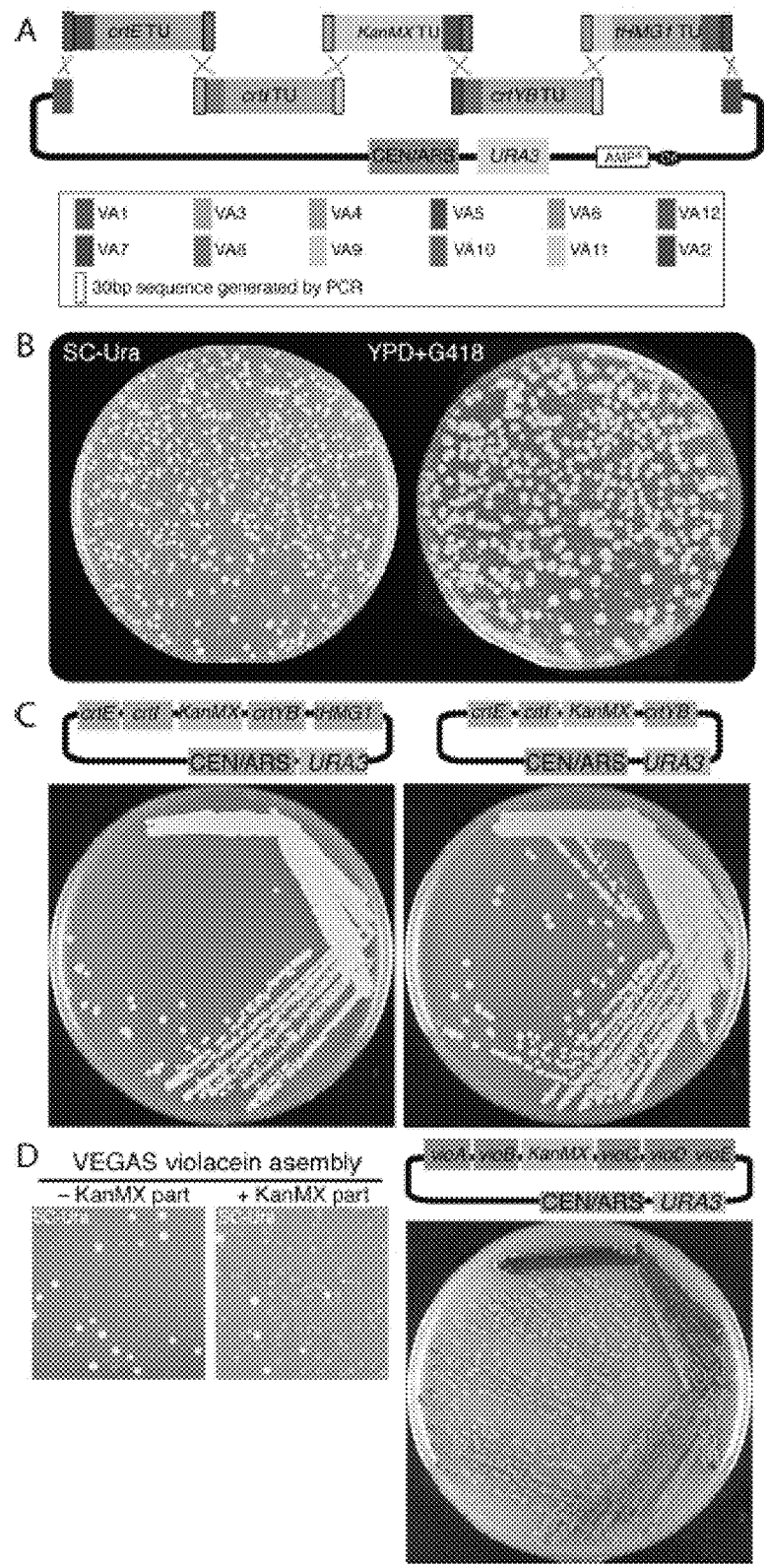
FIG. 11. VEGAS with PCR-mediated homology to assemble the β-carotene and violacein pathways in *S. cerevisiae*. (A) The four β-carotene pathway genes (crtE, crtI, crtYB, tHMG1), assembled as TUs flanked by the indicated VAs (see Table 5 for PRO and TER parts) were subjected to PCR using primers to generate adjacent terminal homology between TUs and the VEGAS assembly vector. (B) *S. cerevisiae* colonies encoding assembled pathways develop a bright yellow color on medium lacking uracil (SC-Ura; left panel) as well as on YPD medium supplemented with G418 (right panel). (C) Re-streaked single colonies from three VEGAS assembly experiments. Left panel: A single yellow colony from the VEGAS assembly experiment in (B) was re-streaked for single colonies. Right panel: by designing a few new primers, a second version of the carotenoid pathway was assembled omitting the tHMG1 TU, generating orange yeast colonies. (D) The violacein pathway assembled in *S. cerevisiae* yields purple colonies.

Example 1 described yGG overhangs for PRO, CDS, and TER parts (FIG. 6) that are highly compatible with gene expression. To enable the VEGAS aspect of this disclosure, we further describe overhang sequences that enable assembly of a VA upstream of the PRO (LVA) and a second VA downstream of the TER (RVA). The overhangs for the LVA part are CCTG-LVA-CAGT and the overhangs for the RVA part are TTTT-RVA-AACT. In one embodiment, a complete structure of a VA-flanked TU assembled by yGG for VEGAS is as follows: (vector end)-CCTG-LVA-CAGT-PRO-AATG-CDS-TGAG-TER-TTTT-RVA-AACT (other vector end) (FIG. 11). For clarity, the bold letters represent the parts.

VEGAS Adapters.

VEGAS adapters are designed to be orthogonal in sequence with respect to the native *S. cerevisiae* genome. For compatibility with assembly, each VA is subcloned into, for example, a kanamycin-resistance vector flanked by, for example, inward-facing BsaI sites; digestion with BsaI exposes overhangs encoded for yGG-VEGAS assembly. Each VA sequence (Table 3) is subcloned with yGG overhangs for assembly into either the LVA (CCTG-LVA-CAGT) or RVA (TTTT-RVA-AACT) position. As a result, each VA sequence can be assigned for assembly into either the LVA or RVA TU position in any modified yGG reaction. Our collection of VEGAS adapter sequences (Table 3) currently contains 18 unique VA sequences, each 57 bases in length (Table 3). The VA collection can easily be expanded by designing new orthogonal sequences by those skilled in the art given the benefit of the present disclosure. Two considerations for designing additional VA sequences include: (i) the sequence must not contain BsaI or BsmBI sites (or any other type IIS restriction sites that may be used for TU assembly) or sites for enzymes used subsequently to release the assembled TU from the yGG acceptor vector (e.g. FseI or NotI)); (ii) the sequence must be distinct from the *S. cerevisiae* genome.

yGG Acceptor Vector Designed for Assembling VA-Flanked TUs.

We have constructed acceptor vectors with a custom multiple cloning site (MCS) for assembly of VA-flanked TUs. These vectors derive from pUC19, with all pre-existing instances of BsaI and BsmBI restriction sites removed to support the function of the newly installed, custom MCS, which is dependent on the sequential action of these two enzymes. The MCS encodes a detectable marker, for example, an RFP cassette with an *E. coli* promoter and terminator sequences that confer a red colony color upon introduction into *E. coli*. The RFP cassette is flanked by outwardly facing BsaI sites that expose the required VA overhangs for yGG assembly (LVA 5' end: CCTG; RVA 3' end: AACT). Successful yGG assembly cuts the RFP cassette out of the plasmid allowing identification of positive clones by white/red screening. Finally, beyond each BsaI site is encoded an inward facing BsmBI site that can be used to release assembled TUs for subsequent VEGAS assembly. For assemblies that are incompatible with BsmBI digestion to release the assembled TU (for example if any of the parts encode an internal BsmBI site), we have also built additional vectors that use NotI or FseI, two rare cutters with 8 bp recognition sequences, to release assembled TUs flanked by VAs. In principle any enzyme that does not cut internally to the assembly VA-flanked TU can be built into this acceptor vector, and use of all of such enzymes is encompassed by this disclosure.

VEGAS to Assemble Pathways for Expression in Yeast.

Figure 7:
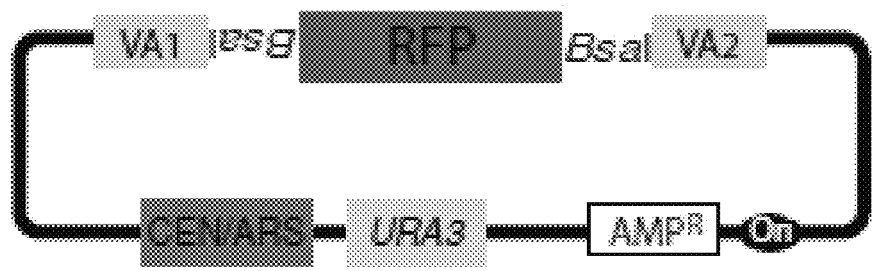
FIG. 7. VEGAS vector for pathway assembly. Digestion with BsaI linearizes the VEGAS assembly vector, releasing an RFP cassette and exposing terminal VA sequences VA1 and VA2 on the vector arms. Assembly of a genetic pathway by homologous recombination in yeast is selected on medium lacking uracil based on expression of URA3 from the vector backbone and mitotic stability in dividing yeast cells ensured based on the centromere (CEN) and autonomously replicating sequence (ARS) combination encoded on the vector. The VEGAS assembly vector also encodes resistance to ampicillin ($AMP^R$) plus an *E. coli* replication origin (Ori); assembled constructs can therefore be recovered from yeast into *E. coli*.
Figure 9:
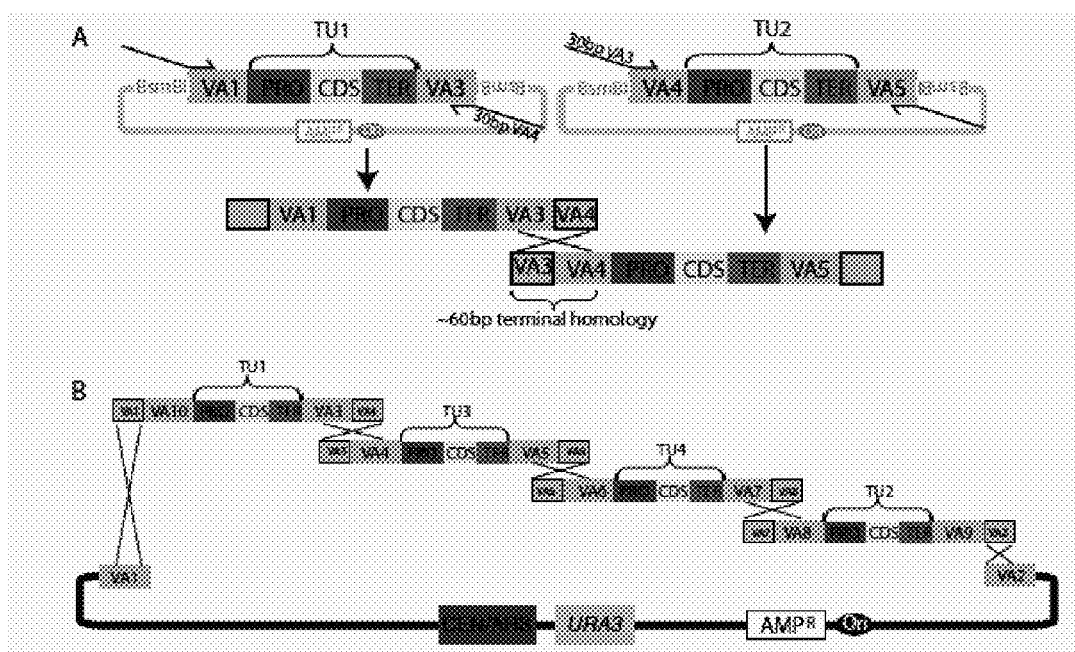
FIG. 9.

The VAs flanking each assembled TU comprise a condition for implementing VEGAS. Specifically, each VA provides 57 bp of unique sequence that can be leveraged for homologous recombination-dependent pathway assembly in vivo into a specially designed VEGAS acceptor vector (FIG. 7). This approach supports modularity during assembly and re-usability of parts, thereby allowing combinatorial assembly of TUs. We have developed two illustrative and distinct VEGAS workflows that are described below. Briefly, in the first instance the VAs themselves provide terminal sequence homology for pathway assembly (FIG. 8), while in the second instance the VAs serve as primer binding sites for overhang extension PCR to generate terminal homology (FIG. 9). The latter workflow has as an advantage that the order and orientation of genes in the pathway can be changed even after TU assembly simply by designing new sets of primers. In both cases, a common VEGAS vector is used for pathway assembly.

VEGAS Vector.

In an embodiment, a VEGAS vector (FIG. 7) is used for pathway assembly by homologous recombination in *S. cerevisiae*. It encodes all sequences required for mitotic stability in yeast, including a centromere (CEN), replication origin (autonomously replicating sequence (ARS)), and a selectable marker. A 2 micron origin can also be used in place of the CEN/ARS combination. Because the final assembled construct in yeast is circular, there is no requirement for telomeres. Further, the vector encodes a selectable marker and replication origin for propagation in *E. coli*. Our VEGAS assembly vector design includes a custom multiple cloning site (MCS) in which an *E. coli* RFP expression cassette is flanked by outward facing BsaI sites; all other instances of BsaI sites have been recoded or removed from the vector. Digestion with BsaI linearizes the vector, releasing the RFP cassette and exposing previously incorporated terminal VA sequences (VA1 and VA2). MCSs are included in this disclosure.

VA Homology VEGAS.

In an embodiment, the order and orientation of all pathway genes is defined at the outset and VAs are assigned to each TU based on the selected position. Specifically, the LVA assigned to the left-most positioned TU encodes a VA sequence '1' (VA1, Table 3) to match one end of the linearized VEGAS assembly vector (see above); adjacent TUs encode identical VA sequences assembled in the RVA and LVA positions; finally the RVA of the right-most TU encodes VA sequence '2' (VA2, Table 3) to match the other end of the linearized VEGAS assembly vector (FIG. 7). The TUs of the pathway of interest are assembled in individual reactions, and following *E. coli* transformation and isolation of a correctly assembled construct (white colony), the VA-flanked TU inserts can be released by, for example, BsmBI digestion (FIG. 8A). The digestion products corresponding to all pathways TUs can then be transformed into yeast along with the linearized VEGAS assembly vector and the pathway assembled by homologous recombination (FIG. 8B). In this scenario, gene order and orientation in the assembled pathway are fixed once the yGG reactions are performed. The position of TUs with respect to one another can only be changed if the TUs are reassembled by yGG with newly assigned VAs.

PCR-Mediated VEGAS.

In this approach, which is encompassed in the disclosure, a unique VA sequence (Table 3) is assigned to the LVA and RVA positions of each TU in the genetic pathway. As a result, the yGG-assembled VA-flanked TUs encode no terminal sequence homology with one another or with the VEGAS assembly vector. Rather, each assembled TU is subjected to PCR amplification using primers that anneal to the VAs and encode specific overhangs that generate terminal sequence homology between adjacent TUs (and the vector). An advantage to this workflow is the capability to change the gene order and orientation without having to rebuild each TU, as described above.

Proof-of-Concept: yGG and VEGAS to Assemble the β-Carotene and Violacein Pathways in *S. cerevisiae*.

The four gene β-carotene pathway and the five gene violacein pathway serve as useful tools to develop DNA assembly strategies as pathway expression can be tracked by the development of colored yeast. Expression of violacein pathway genes (vioA, vioB, vioC, vioD, and vioE from *Chromobacterium violaceum* can turn yeast purple, while expressing genes of the β-carotene pathway (crtE, crtI, crtYB from *Xanthophyllomyces dendrohous*) yields orange colonies. Color production in both cases is quantitatively and qualitatively dependent on pathway flux and thus on the expression levels of pathway genes. For instance, overexpression of the catalytic domain of the *S. cerevisiae* HMG CoA reductase HMG1 (tHMG1) can dramatically alter carotenoid production, yielding yellow colonies. As proof-of-concept of the VEGAS methodology we have assembled carotenoid and violacein pathways for expression in *S. cerevisiae* using yGG-assembled VA-flanked TUs.

VA Homology.

Figure 10:
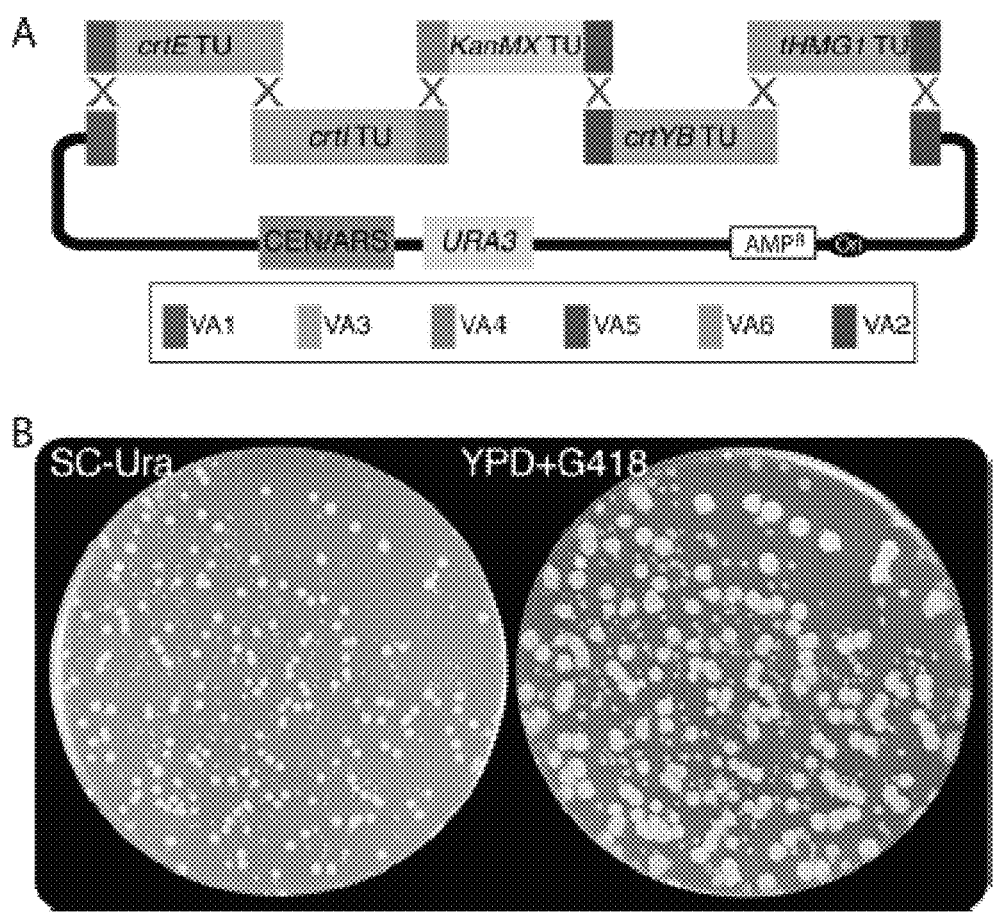
FIG. 10. VEGAS with adapter homology to assemble the carotenoid pathway in *S. cerevisiae*. (A) The four β-carotene pathway genes (crtE, crtI, crtYB, tHMG1), assembled as TUs flanked by the indicated VAs (see Table 4 for PRO and TER parts) were released from the yGG acceptor vector with BsmBI digestion and co-transformed into yeast with the linearized VEGAS assembly vector. (B) *S. cerevisiae* colonies encoding assembled pathways develop a bright yellow color on medium lacking uracil (SC-Ura; left panel) as well as on YPD medium supplemented with G418 (right panel).

To demonstrate VEGAS using terminal homology encoded in the VA sequences, we assigned each β-carotene pathway CDS a unique *S. cerevisiae* promoter and terminator (Table 4) and pre-determined the desired, left-to-right assembly order (FIG. 10A). A strong promoter was assigned to each CDS for high expression of each gene. In the VEGAS experiments presented here we included the KanMX TU (pre-assembled as a PRO-CDS-TER yGG part), whose protein product yields resistance to the drug G418, to permit a secondary plate-based screening approach using an unselected marker to test for efficiency of correct assemblies in yeast. Based on the pre-defined gene assembly order (FIG. 10A) we assigned the appropriate LVA and RVA to each TU. Subsequent to yGG, a correctly assembled TU (white colony) for each of the five reactions was selected and the pathway assembled by VEGAS via co-transformation of BsmBI-digested TUs plus the linearized VEGAS assembly vector. The primary selection for assembly was carried out on medium lacking uracil (SC-Ura), as the URA3 gene was encoded on the assembly vector (FIG. 5A). Almost all colonies growing on the SC-Ura plate were yellow in color, consistent with assembly of a functional pathway that includes tHMG1 (13) (FIG. 10B, left panel). Moreover, following replica plating onto YPD medium supplemented with G418, virtually 100% of colonies were G418 resistant as expected for 100% correct assembly (FIG. 10B, right panel). The variation in color (light yellow versus darker yellow or even orange) between colonies may result from stochasticity in expression of pathway genes between colonies, mis-assembly (for instance absence of tHMG1 TU, see below), or variation in plasmid copy number (e.g. two copies versus one); indeed the yellow colony color typically normalizes across the plate with incubation for several more days.

PCR-Mediated Homology.

In this approach, which is encompassed in this disclosure, unique VA sequences were assigned to the LVA and RVA position for each of the 4 β-carotene pathway TUs plus the KanMX TU (Table 5). The promoter and terminator parts for each CDS as well as the defined left-to-right gene order were not changed as compared to the adapter homology experiment described previously (Table 4 compared to Table 5). Following yGG assembly, the reaction mixtures were used directly for five independent PCRs to amplify each TU with primers encoding ~20 nucleotides (nt) of sequence to anneal to the VA plus ~30 nt of assigned neighboring homology sequence; together this yielded ~50 bp of terminal homology between adjacent parts for VEGAS (FIG. 11A). The PCR products were co-transformed along with the linearized VEGAS assembly vector into yeast and selection for assembly was carried out on SC-Ura medium. Here ~95% of colonies developed a yellow color on SC-Ura and virtually 100% of colonies were also G418 resistant (FIG. 11B). Compared to the adapter-mediated homology assembly (FIG. 10B), more colonies appeared white in color (~5% compared to ~1% in FIG. 10B) and most of these were also G418 resistant, suggesting a slightly lower fidelity of assembly in this approach. When a single yellow-colored, Ura+, G418ʳ colony was restreaked on YPD medium supplemented with G418, all resulting colonies were of a uniform yellow color (FIG. 11C, left panel). The assembled pathway from this colony was recovered into *E. coli* and the plasmid structure confirmed by digestion and sequencing (data not shown).

To demonstrate versatility of the PCR-mediated VEGAS approach, we assembled a different version of the β-carotene pathway, this time omitting the tHMG1 TU. To accomplish this, we re-used the previously yGG assembled, VA-flanked TUs for crtE, crtI, KanMX marker, and crtYB, and simply amplified the crtYB TU with a different primer encoding terminal homology to the VEGAS (FIG. 11C, right panel). Transformation plates resembled those shown in FIG. 11B but the assembly yielded colonies producing an orange color (FIG. 11C, right panel). The structure of assemblies producing orange yeast cells was validated by recovery into *E. coli* and digestion (data not shown).

In another embodiment, we constructed the violacein pathway using PCR-mediated VEGAS of the five violacein TUs plus the KanMX cassette; together this was a seven-piece assembly including the vector backbone. TUs were assembled with flanking VAs by yGG (Table 6), and terminal homology between adjacent parts was introduced by PCR. Transformation into yeast of all parts required for pathway assembly, as compared to a control experiment omitting the KanMX part, yielded a substantial increase in the number of colonies producing a purple pigment on the primary SC-Ura transformation plates (FIG. 11D). This color developed in all colonies upon re-streaking (FIG. 11D). White colonies may arise from mis-assemblies or from circularization of the parental, empty VEGAS vector. The structure of assemblies producing purple yeast colonies was validated by recovery into *E. coli* and digestion, and was found to be correct in 7/7 independent colonies (data not shown).

yGG and VEGAS for Combinatorial Pathway Assembly

An advantage of VEGAS is its compatibility with combinatorial assembly, made possible by the modularity provided by the VA sequences. To demonstrate this, we generated combinatorial transcription unit (TU) libraries for each of the four β-carotene pathway genes and then used PCR-mediated VEGAS to assemble the TU libraries into combinatorial pathways for expression in yeast. With a pool of 10 promoters and 5 terminators in each TU combinatorial assembly (Table 7), the theoretical library complexity exceeded 60,000 possible combinations. For this experiment the 5 TUs were assigned the same VAs as in Table 5, so the same primers were used to generate amplicons with terminal homology. Following VEGAS in *S. cerevisiae*, we observed a wide diversity of colony colors on the transformation/G418 replica plate (FIG. 12A). We interrogated the stability and robustness of expression of the assembled pathways by re-streaking transformants representing many different colors for single colonies (FIGS. 12B and C.) Sequence analysis of five constructs conferring uniquely colored yeast colonies (orange, bright yellow, light pink, light yellow, white) revealed the presence of all 10 promoters and 4 of the 5 terminators in at least one position in an assembled pathway, consistent with unbiased combinatorial assembly reactions (FIG. 12E-H). Finally, we assessed the production of three carotenoid compounds in yeast cells expressing four unique β-carotene pathways (strains from FIG. 12D-G). Indeed, we observed different abundances of β-carotene, phytoene, and lycopene in these strains (FIG. 12I). While each of the yellow and orange strains produce two to three times more β-carotene than the pink colored strain, it is likely the abundance of lycopene that differentiates the orange from the yellow strain. On the other hand both yellow strains produce an abundance of phytoene, an early intermediate in the β-carotene pathway, suggesting flux could still be improved by additional pathway engineering; alternatively, additional transformants could be screened to identify assembled pathways that yield higher β-carotene titres.

Biosynthetic pathways typically consist of multiple genes whose individual protein products function much like an assembly line, converting an initial substrate, through some number of intermediate steps, into a desired end product. Expressing biosynthetic pathways in *S. cerevisiae*, in particular those not natively encoded in the *S. cerevisiae* genome, is desirable as it effectively converts this microorganism into a cellular factory capable of producing valuable compounds. A major consideration is tuning expression of individual genes to optimize flux through the pathway, given that balanced gene expression can often trump simple overexpression of each pathway gene with respect to yield. High-level constitutive expression may create a significant metabolic burden on the cell, or lead to the accumulation of toxic foreign intermediates. For example, violacein is toxic to yeast cells at high concentration (22), which may contribute to the slower growth of purple colonies as compared to white ones on the VEGAS violacein assembly plates (FIG. 11D).

Figure 12:
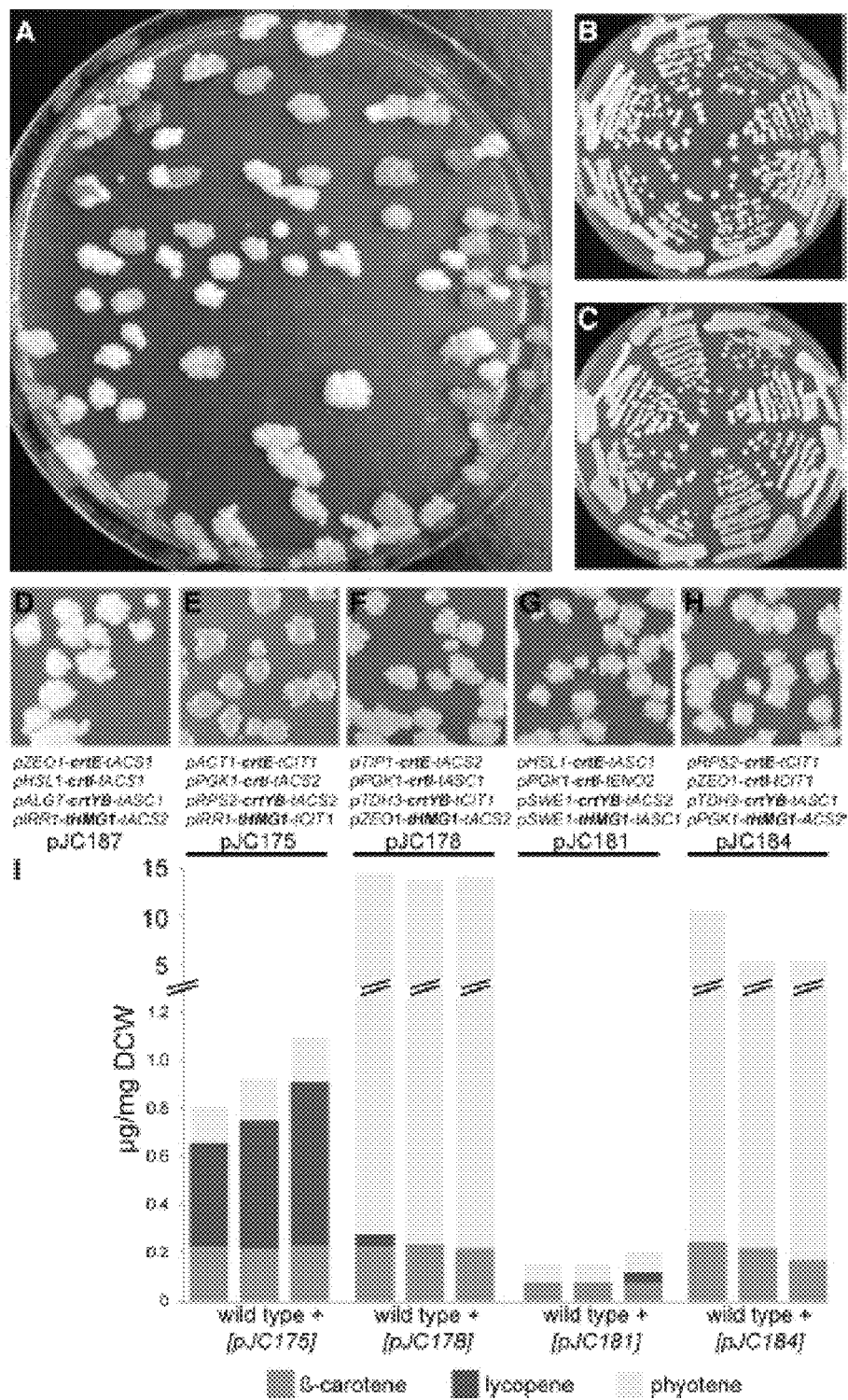
FIG. 12. Combinatorial assembly of the β-carotene pathway in *S. cerevisiae*. (A) Combinatorial TU libraries of the four β-carotene pathway genes (crtE, crtI, crtYB and tHMG1), were generated by yeast Golden Gate and assembled for expression in yeast by VEGAS as in FIG. 11 except with pools of 10 PRO and 5 TER parts for each yGG assembly of each TU. Transformants of varying colors reflect production of different levels of β-carotene and its intermediates due to varied expression of all genes in the pathway leading to different concentrations of both end product and intermediates. (B and C). Single colony purification of transformants in (A). (D-H). Five assembled constructs were recovered from yeast into *E. coli* (pJC175, pJC178, pJC181, pJC184, and pJC187) and sequenced to identify the promoters and terminators driving expression of each pathway gene. Each construct was also re-transformed into yeast to verify production of β-carotene (and intermediates) based on the yeast colonies developing color uniformly. Shown are replica plates on YPD supplemented with G418. (I). HPLC quantification of carotenoids produced in strains FIG. 12E-H. In all cases ~12.5 g of yeast (dry cell weight (DCW)) was used for the analysis. Quantification was performed in biological triplicate for each strain as shown. All strains analysed contained additional carotenoid peaks that may have contributed to color formation.

It will be apparent from the foregoing that in the present disclosure we address the challenge of assembling and tuning genetic pathways with VEGAS, a modular approach that allows facile assembly of TUs flanked by VEGAS adapters (VAs) into complete genetic pathways by homologous recombination in yeast. Gene expression can be controlled by assigning desired regulatory elements (PRO and TER parts) up front or, as we demonstrate for the β-carotene pathway, in a combinatorial manner. Many previous studies investigating the expression of β-carotene expression in *S. cerevisiae* have relied on a previously built construct encoding crtE, crtI, and crtYB, each expressed using an identical promoter and terminator combination. Here, using VEGAS/yGG we construct and characterize six new β-carotene pathway expression cassettes; in principle we could characterize any number of additional constructs assembled using the combinatorial approach. These constructs represent useful new resources since they display a high degree of genetic stability in yeast, evidenced by the uniformity of colony color (FIGS. 11 and 12). Presumably the observed genetic stability is a function of the use of unique promoters and terminators flanking each CDS. Notably, the constructs derived from the combinatorial assembly share at least one common part (FIG. 12D-H); based on this disclosure, in future combinatorial assembly experiments, this could easily be overcome by increasing the number of PRO and TER parts used during combinatorial assembly.

VEGAS specifies episomal expression of the assembled genetic pathway, which comes with certain qualities. Episomal expression allows one to leverage a variety of systematic screening tools available for *S. cerevisiae*, for instance the deletion mutant collection or the overexpression array, since the pathway can easily be moved between strains. Moreover, state-of-the art approaches such as SCRaMbLE) of synthetic chromosomes (constructed as part of the Sc2.0 Synthetic Yeast Genome Project (www.syntheticyeast.org), can be implemented to identify favorable genetic backgrounds for pathway expression. However, the use of selective medium or the addition of a drug to ensure maintenance of the pathway construct may lead to decreased product yield. One solution is to make the plasmid essential in the strain background such that it cannot be lost; this approach could be implemented either as part of the VEGAS workflow, or at a later date once the desired construct is introduced into the most favorable strain background. Of course, a VEGAS assembly vector could also be constructed (or retrofitted) such that following episomal VEGAS pathway assembly and characterization the pathway could be integrated into the genome, given the benefit of this disclosure.

The use of computationally derived orthogonal sequences provides a powerful tool for DNA assembly, as described here using yeast and elsewhere using in vitro methods. *S. cerevisiae*, with its inherent capacity for homologous recombination, is a useful cloning tool; the standardized and modular assembly of genetic pathways by yGG/VEGAS need not be limited to expression in *S. cerevisiae*. Rather, pathways assembled episomally in yeast using this approach can easily be transferred to other microorganisms, in particular those that are not proficient at homologous recombination.

EXAMPLE 3

The following materials and methods were used to obtain the results described above. One-pot yGG Assembly. TU parts (PRO, CDS and TER), each subclone cloned into a Kanamycin resistant vector (pCR Blunt II TOPO, Invitrogen/Life technologies, Carlsbad, Calif. 450245), were combined in equimolar amounts and mixed with Reaction Master Mix [1.5 µl 10×T4 DNA ligase reaction buffer (New England Biolabs, M0202), 0.15 µl 100× Bovine Serum Albumin (BSA, New England Biolabs), 600 U T4 DNA ligase (rapid) (Enzymatics, Beverly, Mass., L6030-HC-L) and 10 U or 100 U of BsaI or/and BsmBI (New England Biolabs, Beverly, Mass., R0535 or R0580, respectively)] to a final volume of 15 µL. The high concentration BsaI was a custom order from New England Biolabs. One-pot digestion-ligation assembly was performed in a thermo-cycler as follows: 25 cycles of 37° C. for 3 min and 16° C. for 4 min, followed by 50° C. for 5 min and 80° C. for 5 min. 5 µL of each assembly reaction was transformed into 50 µL of competent DH5a *E. coli* cells and plated on the appropriate selection media. For C-terminal tagging yGG assembly reactions, before the one-pot yGG assembly, 1 µg of cloned CDS was digested with BceAI, loaded on a gel and the appropriate band was extracted (Zymo Research, Irvine, Calif.).

Design of VEGAS Adapter Sequences.

From a previously generated, in-house collection of 10mer sequences that rarely occur in the *S. cerevisiae* genome, 60mers were randomly produced by concatenation in silico. The eighteen 60mers with the lowest similarity to the *S. cerevisiae* genome were selected to comprise the initial set of VA sequences reported here. For cost minimization, the VA sequences were subsequently shortened to 57mers by deleting three terminal base pairs (Table 3). Alternatively, the web-based tool R2oDNA can be used to design orthogonal sequences for use as VA sequences, given the benefit of the present disclosure.

Vector Construction.

To construct the yGG acceptor vector for TUs destined for VEGAS, pUC19 was modified using a known approach. Briefly, all pre-existing instances of BsaI and BsmBI sites were re-coded or deleted and a custom multiple cloning site was installed, encoding an *E. coli* RFP expression cassette flanked by outward-facing BsaI sites designed to leave 5' and 3' VA designer overhangs (top strand: CCTG and AACT, respectively). Additionally, neighboring NotI and FseI sites, or inward-facing BsmBI sites were further encoded outside of the BsaI sites to facilitate excision of assembled VA-flanked TUs from the construct. Plasmid identification numbers are: pNA0178 (NotI and FseI) and pJC120 (BsmBI). To construct the VEGAS assembly vector, a previously constructed yGG acceptor vector (11), pAV116, which derives from pRS416 (12), was used. VA1 and VA2 sequences, plus BsaI sites (as shown in FIG. 7) were then introduced up and downstream of an *E. coli* RFP expression cassette.

Parts Cloning.

The β-carotene CDS parts crtE, crtI, and crtYB, were amplified from genomic DNA of an *S. cerevisiae* strain previously engineered to express the pathway (13). Codon optimized violacein biosynthetic enzyme CDS parts, vioA, vioB, vioC, vioD, and vioE, were synthesized. The truncated version of HMG1 (tHMG1) plus all PRO and TER parts were amplified from genomic DNA extracted from the BY4741 strain of *S. cerevisiae*. Primers used for amplification included overhangs encoding inward-facing BsaI sites separated by one base from the appropriate yGG-compatible overhangs. All parts were subcloned using the Zero Blunt TOPO PCR cloning kit (Life Technologies; 45-0245), transformed into *E. coli* (Top10 cells), and sequence verified. CDS parts that encoded BsaI or BsmBI sites were re-coded by Multichange Isothermal mutagenesis (MISO) using an established approach. All parts and their corresponding sequence files are available upon request.

Yeast Golden Gate (yGG) into the VEGAS yGG Acceptor Vector.

100 ng of yGG acceptor vector (pJC120 for all experiments described in this work) plus equimolar amounts of each part for assembly (LVA, PRO, CDS, TER, RVA) were combined in a Golden Gate reaction consisting of: 1.5 µL 10×T4 DNA ligase reaction buffer (New England Biolabs, M0202), 0.15 µL 100× Bovine Serum Albumin (BSA, New England Biolabs), 600 U T4 DNA ligase (rapid) (Enzymatics, L6030-HC-L) and 10 U of BsaI (New England Biolabs, R0535) in a final volume of 15 µL. One-pot digestion-ligation assembly was carried out in a thermocycler by performing 25 cycles of [37° C. 3 min, 16° C. 4 min], followed by 50° C. 5 min, and 80° C. 5 min. We have also described above several modifications to improve the efficiency of yGG. For 'terminal homology VEGAS' experiments, 5 µL of each yGG reaction was transformed into Top10 *E. coli* and plated on LB plates supplemented with carbenicilllin (75 µg/ml). White colonies were selected for verification of assembly constructs by restriction digest. For combinatorial assembly, PRO or TER parts were mixed in equal molar amounts prior to yGG assembly.

Terminal Homology VEGAS.

~1 µg of yGG-assembled, VA-flanked TU constructs were digested with BsmBI (New England Biolabs, R0580) in a final volume of 20 µL. 2 µL (~100 ng) of each digestion product was used directly for yeast transformation along with ~50 ng of BsaI-linearized VEGAS assembly vector (pJC170 for all experiments described in this work). Yeast transformations were carried out using established approaches except cells were heat shocked for only 15 minutes in the presence of 10% DMSO at 37° C. and prior to plating were incubated in 400 μL of 5 mM CaCl$_2$ for 10 minutes at room temperature. For all VEGAS yeast transformations, following primary selection on SC-Ura plates (incubated 3 days at 30° C.), plate images were taken and transformation plates were replica plated onto YPD medium supplemented with G418 (200 μg/mL). A second set of plate images was taken three days post-replica plating.

PCR-Mediated VEGAS.

Primers were designed to anneal to the leftmost and rightmost ends of the LVA and RVA sequences, respectively. Each primer additionally encoded 30 bp of overhang sequence homologous to the adjacent VA sequence. 1 μL of each yGG reaction was used directly in a PCR reaction with Phusion High-Fidelity DNA Polymerase (M0530L) to amplify the VA-flanked TU and incorporate neighboring homology. 5 μL of each PCR reaction was transformed directly into yeast along with ~50 ng of BsaI-linearized VEGAS assembly vector (pJC170 for all experiments described in this work). Yeast transformation and replica plating steps were performed as described in the "Terminal Homology VEGAS" section.

Plasmid Recovery from Yeast.

Following VEGAS, assembled constructs encoding the β-carotene and violacein pathways were recovered from yeast using an established approach except that in all cases constructs were recovered from 3 mL of cultured yeast (SC-Ura), inoculated from a single yeast colony, and the blue-white E. coli screening step following transformation was omitted. For combinatorial assembly of the β-carotene pathway, PRO and TER parts flanking each CDS were determined by Sanger sequencing of the recovered plasmid.

Carotenoid Production.

Four constructs encoding β-carotene pathways (pJC175, orange; pJC178, bright yellow; pJC181, pink; pJC184, light yellow), each a product of combinatorial PCR-mediated VEGAS (FIG. 9E-H), were used. Three independent colonies of each were inoculated into 10 mL of YPD medium supplemented with G418 (200 μg/mL) and grown to saturation (3 days at 30° C., 250 rpm). Carotenoids were extracted using a PRECELLYS® 24 high-throughput tissue homogenizer. Briefly, 1 mL of culture was pelleted in a PRECELLYS tube and the pellet was extracted with 1 mL tetrahydrofuran (containing 0.01% butylhydroxytoluene (BHT)) by homogenization for 3×15 seconds at 6500 rpm. Following centrifugation for five minutes at 4° C., 800 μL was then transferred to a glass vial. Extracts were dried down and resuspended in 80 μL dichloromethane followed by 720 μL of a 50:50 (v/v) mixture of heptane and ethyl acetate (containing 0.01% BHT). HPLC analysis of carotenoids was performed using standard techniques.

TABLE 1

Standardized prefix and suffix sequences for yGG.

|     | BsaI prefixes | BsaI suffixes | BsmBI prefixes | BsmBI suffixes |
|-----|---------------|---------------|----------------|----------------|
| PRO | GGTCTCA CAGT (SEQ ID NO: 4) | AATGCGA GACC (SEQ ID NO: 5) | CGTCTCA CAGT (SEQ ID NO: 6) | AATGCGA GACG (SEQ ID NO: 7) |
| CDS | GGTCTCA AATG (SEQ ID NO: 8) | TGAGCGA GACC (SEQ ID NO: 9) | CGTCTCA AATG (SEQ ID NO: 10) | TGAGCGA GACG (SEQ ID NO: 11) |
| TER | GGTCTCA TGAG (SEQ ID NO: 12) | TTTTCGA GACC (SEQ ID NO: 13) | CGTCTCA TGAG (SEQ ID NO: 14) | TTTTCGA GACG (SEQ ID NO: 15) |

Bold face 6 bp sequences are recognition sites;

Italicized 4 base sequences are overhang sites.

All sequences are written 5' to 3' on the "top strand" of the final part.

TABLE 2

Acceptor vectors

| Plasmid name | Yeast marker (organism) | Yeast replication parts | Yeast integrative locus | E. coli marker | 2°RE$_b$ | Plasmid number | Addgene ID |
|---|---|---|---|---|---|---|---|
| CEN/ARS (low copy) | | | | | | | |
| pAV113 | HIS3 (Sc) | CEN/ARS | n/a | Amp | n/a | pLM108 | 63180 |
| pAV114 | TRP1 (Sc) | CEN/ARS | n/a | Amp | n/a | pLM264 | 63181 |
| pAV115 | LEU2 (Sc) | CEN/ARS | n/a | Amp | n/a | pLM109 | 63182 |
| pAV116 | URA3 (Sc) | CEN/ARS | n/a | Amp | n/a | pLM304 | 63183 |
| pAV11K | KanMX | CEN/ARS | n/a | Amp | n/a | pLM200 | 63184 |
| pAV113.loxP$_a$ | HIS3 (Sc) | CEN/ARS | n/a | Amp | n/a | pJC081 | 63186 |
| pAV115.loxP$_a$ | LEU2 (Sc) | CEN/ARS | n/a | Amp | n/a | pJC082 | 63187 |
| pAV116.loxP$_a$ | URA3 (Sc) | CEN/ARS | n/a | Amp | n/a | pJC106 | 63188 |
| 2 micron (μ) (high copy) | | | | | | | |
| pAV123 | HIS3 (Sc) | 2μ | n/a | Amp | n/a | pAM090 | 63189 |
| pAV124 | TRP1 (Sc) | 2μ | n/a | Amp | n/a | pLM266 | 63190 |
| pAV125 | LEU2 (Sc) | 2μ | n/a | Amp | n/a | pLM270 | 63191 |
| pAV126 | URA3 (Sc) | 2μ | n/a | Amp | n/a | pAM078 | 63192 |
| Integrative | | | | | | | |
| pAV103 | HIS3 (Sc) | n/a | HIS3 | Amp | n/a | pLM346 | 63193 |
| pAV104 | TRP1 (Sc) | n/a | TRP1 | Amp | n/a | pLM262 | 63194 |
| pAV105 | LEU2 (Sc) | n/a | LEU2 | Amp | n/a | pLM107 | 63195 |
| pAV106 | URA3 (Sc) | n/a | URA3 | Amp | n/a | pLM302 | 63196 |

TABLE 2-continued

Acceptor vectors

| Plasmid name | Yeast marker (organism) | Yeast replication parts | Yeast integrative locus | E. coli marker | 2°RE[b] | Plasmid number | Addgene ID |
|---|---|---|---|---|---|---|---|
| pAV10.F3 | HIS3 (Sc) | n/a | chrVI: 97873-98803 | Cam | NotI or BciVI | pSIB055 | 63199 |
| pAV10.F3.loxP[a] | HIS5 (Sp) | n/a | chrVI: 97873-98803 | Amp | NotI | pSIB581 | 63200 |
| pAV10.F6.loxP[a] | URA3 (Kl) | n/a | chrVI: 97873-98803 | Amp | NotI or BciVI | pSIB582 | 63201 |
| pAV10.K3.loxP[a] | HIS5 (Sp) | n/a | YKL162C-A | Amp | NotI | pSIB584 | 63202 |
| pAV10.K6.loxP[a] | URA3 (Kl) | n/a | YKL162C-A | Amp | NotI or BciVI | pSIB585 | 63203 |
| pAV10.K5.loxP[a] | LEU2 (Sc) | n/a | YKL162C-A | Amp | NotI or BciVI | pSIB586 | 63204 |
| pAV10.HO3.loxP[a] | HIS5 (Sp) | n/a | HO locus | Amp | NotI | pSIB587 | 63205 |
| pAV10.HO5.loxP[a] | LEU2 (Sc) | n/a | HO locus | Amp | NotI or BciVI | pSIB589 | 63206 |
| pAV10.K3 | HIS5 (Sp) | n/a | YKL162C-A | Amp | NotI | pSIB596 | 63207 |
| pAV10.KH | hygromycin | n/a | YKL162C-A | Amp | NotI | pSIB599 | 63208 |
| pAV10.KN | cloNAT | n/a | YKL162C-A | Amp | NotI | pSIB601 | 63209 |
| pAV10.K5 | LEU2 (Sc) | n/a | YKL162C-A | Amp | NotI or BciVI | pSIB604 | 63210 |
| pAV10.HO6 | URA3 (Kl) | n/a | HO locus | Amp | NotI or BciVI | pSIB843 | 63211 |
| pAV10.K4 | TRP1 (Sc) | n/a | chrIXR: 387328-388330 | Amp | n/a | pKF091 | 63212 |
| pAV10 | n/a | n/a | n/a | Amp | NotI or FseI | pNA0179 | 63213 |

[a] ".loxp' indicates the inclusion of loxp sites in the yGG vector. The TU is flanked by two Loxp sites.
[b] "2°RE" refers to the secondary restriction enzyme used to release an assembled TU prior to integrative yeast transformation.
Sc, *Saccharomyces cerevisiae*;
Sp, *Schizosaccharomyces pombe*;
Kl, *Kluyveromyces lactis*;
Amp, ampicillin;
Cam, *chloramphenicol*.
For additional information on yGG acceptor vector nomenclature see FIG. 2.

TABLE 3

VEGAS adapter sequences

| Name | Sequence (5'-3') |
|---|---|
| VA1* | CCCCTTAGGTTGCAAATGCTCCGTCGACGGGATCTGTCCTTCTCTGCCGGCGATCGT (SEQ ID NO: 1) |
| VA2** | TGACGCTTGGATGCGTGACCCCGTACGTCATGACCCGTCATGGGTATGTAAGCGAAG (SEQ ID NO: 2) |
| VA3 | GGAGGTACTGGCCTAGCGTCGTGGCCCGGGAGAGACAGTTTAGTAGTGACTCGCGGC (SEQ ID NO: 16) |
| VA4 | TTGGCGTTAATTGTAGCTTATTTCCCGCCCTGTGATTGAGGCGGGATGGTGTCCCCA (SEQ ID NO: 17) |
| VA5 | GACTAAGACTCTGGTCACGGTTCAGAAGTGGACGATGCATGTCGTCGGGCTGATAGA (SEQ ID NO: 18) |
| VA6 | TGCACGGCGCTAGGTGTGATATCGTACACTTGGGAGAAGTCAGATACGATTGCGCT (SEQ ID NO: 19) |
| VA7 | TAGCGGCGCCGGGAAATCCAGCATATTCTCGCGGCCCTGAGCAGTAGGTGTCTCGGG (SEQ ID NO: 20) |
| VA8 | GAGTCTACGTTACACCTGAACTCGCATGTCTGGGGTTGTGGTCAGGCCTTGTCAATT (SEQ ID NO: 21) |
| VA9 | GCGTACTGGCCGCCCGGGCCTGATGTGGCCGTCCTATTAGCATTGTACACCCTCATT (SEQ ID NO: 22) |
| VA10 | CTTGAATCGGCTTTAGGATCCGGTACTGCCGACGCACTTTAGAACGGCCACCGTCCT (SEQ ID NO: 23) |
| VA11 | GCAAGTTTTGAAGAGGTGTAAACTCTCCGCAGCACCTCCGGACTATGCCCGAGTGGT (SEQ ID NO: 24) |
| VA12 | TGAAGCTACGCGCCGAGCGTCTGACTCCTTTAGTCCGCGTCATCGCTTTGAGCGCGT (SEQ ID NO: 25) |
| VA13 | TCCGGATCCCTTTCGGTCCATATAGCGGATTTCCATAGACGTAGACCGCGCCAATGT (SEQ ID NO: 26) |
| VA14 | GACGACGCGTTCTGTGTCTTCGTTGCGGCTCTGCGCTTGGTCGTTGGCGACGGCCGT (SEQ ID NO: 27) |
| VA15 | TGTAAGGGCGTCTGTTAACCCAAGGTCCCTCGAACCGTATGCAGAGCCGTGGCTACG (SEQ ID NO: 28) |

TABLE 3-continued

VEGAS adapter sequences

| Name | Sequence (5'-3') |
|---|---|
| VA16 | TATCGCGGGTGCGTGCATCGACAAGCCATGCCCACCT TCTGGTCGATTGGGCTGGCG (SEQ ID NO: 29) |
| VA17 | CATCCATCGATATTTGGCACTGGACCTCAACGCTAGT GTTCGCGGACTGCACTACCT (SEQ ID NO: 30) |
| VA18 | GATTAAGGGGCATACCGTGCCTATCCTGGTAATTGTG TAGGCTACCTGTCTGTATAC (SEQ ID NO: 31) |

*encoded terminally on the left arm of the linearized VEGAS assembly vector
**encoded terminally on the right arm of the linearized VEGAS assembly vector

TABLE 4 yGG parts for adapter homology-mediated assembly of the β-carotene pathway by VEGAS

| TU order (left to right) | LVA | PRO | CDS | TER | RVA |
|---|---|---|---|---|---|
| 1 | VA1 | pTDH3 | crtE | ttACS2 | VA3 |
| 2 | VA3 | pPGK1 | crtI | ttENO2 | VA4 |
| 3 | VA4 | — | KanMX TU | — | VA5 |
| 4 | VA5 | pACT1 | crtYB | ttASC1 | VA6 |
| 5 | VA6 | pRPS2 | tHMG1 | ttCIT1 | VA2 |

TABLE 5 yGG parts for PCR-mediated assembly of the β-carotene pathway by VEGAS

| TU order (left to right) | LVA | PRO | CDS | TER | RVA |
|---|---|---|---|---|---|
| 1 | VA7 | pTDH3 | crtE | ttACS2 | VA3 |
| 2 | VA8 | pPGK1 | CrtI | ttENO2 | VA4 |
| 3 | VA9 | — | KanMX TU | — | VA5 |
| 4 | VA10 | pACT1 | crtYB | ttASC1 | VA6 |
| 5 | VA11 | pRPS2 | tHMG1 | ttCIT1 | VA12 |

TABLE 6 yGG parts for PCR-mediated assembly of the violacein pathway by VEGAS

| TU order (left to right) | LVA | PRO | CDS | TER | RVA |
|---|---|---|---|---|---|
| 1 | VA7 | pTDH3 | vioA | ttACS2 | VA3 |
| 2 | VA8 | pPGK1 | vioB | ttENO2 | VA4 |
| 3 | VA9 | — | KanMX TU | — | VA5 |
| 4 | VA10 | pACT1 | vioC | ttASC1 | V6 |
| 5 | VA11 | pRPS2 | vioD | ttCIT1 | VA12 |
| 6 | VA16 | pZEO1 | vioE | ttFUM1 | VA5 |

TABLE 7

Promoter and terminators pools for combinatorial assembly

| PRO | TER |
|---|---|
| pTDH3 | ttACS2 |
| pPGK1 | ttENO2 |
| pACT1 | ttASC1 |
| pRPS2 | ttCIT1 |
| pZEO1 | ttSIK1 |
| pIRR1 | |

TABLE 7-continued

Promoter and terminators pools for combinatorial assembly

| PRO | TER |
|---|---|
| pALG7 | |
| pSWE1 | |
| pTIP1 | |
| pHSL1 | |

These following parts were used to examine yGG efficiency. BsaI sites are marked in red, overhangs are marked in blue. In both 4 part and 8 part assemblies pAV113 (Table 2) was used as an acceptor vector and the GAL1 promoter and terminator were used with the appropriate overhangs:

>GAL1p
(SEQ ID NO: 31)
ggtctcacagtTGGAACTTTCAGTAATACGCTTAACTGCTCATTGCTA

TATTGAAGTACGGATTAGAAGCCGCCGAGCGGGCGACAGCCCTCCGAC

GGAAGACTCTCCTCCGTGCGTCCTCGTCTTCACCGGTCGCGTTCCTGA

AACGCAGATGTGCCTCGCGCCGCACTGCTCCGAACAATAAAGATTCTA

CAATACTAGCTTTTATGGTTATGAAGAGGAAAAATTGGCAGTAACCTG

GCCCCACAAACCTTCAAATTAACGAATCAAATTAACAACCATAGGATG

ATAATGCGATTAGTTTTTTAGCCTTATTTCTGGGGTAATTAATCAGCG

AAGCGATGATTTTTGATCTATTAACAGATATATAAATGGAAAAGCTGC

ATAACCACTTTAACTAATACTTTCAACATTTTCAGTTTGTATTACTTC

TTATTCAAATGTCATAAAAGTATCAACAAAAAATTGTTAATATACCTC

TATACTTTAACGTCAAGGAGAAAAAACTATAaatgcgagacc

>GAL1t
(SEQ ID NO: 32)
ggtctcatgagGTATACTTCTTTTTTTTACTTTGTTCAGAACAACTTC

TCATTTTTTCTACTCATAACTTTAGCATCACAAAATACGCAATAATA

ACGAGTAGTAACACTTTTATAGTTCATACATGCTTCAACTACTTAATA

AATGATTGTATGATAATGTTTTCAATGTAAGAGATTTCGATTATCCAC

AAACTTTAAAACACAGGGACAAAATTCTTGATATGCTTTCAACCGCTG

CGTTTTGGATACCTATTCTTGACATGATATGACTACCATTTTGTTATT

GTACGTGGGCAGTTGACGTCTTATCATATGTCAAAGTCATTTGCGAA

GTTCTTGGCAAGTTGCCAACTGACGAGATGCAGTAAAAAGAGATTGCC

GTCTTGAAACTTTTTGTCCTTTTTTTTTTCCGGGGACTCTACGAGAAC

CCTTTGTCCTACTGATTAATTTTGTACTGAATTTGGACAATTCAGATT

TTAGTAGACAAGCGCGAGGAGGAAAAGAAATGACAGAAAAATTCCGAT

GGACAAGAAGATAGGAAAAAAAAAAGCTTTCACCGATTTCCTAGACC

GGAAAAAAGTCGTATGACATCAGAATGAAAAATTTTCAAGTTAGACAA

GGACAAAATCAGGACAAATTGTAAAGATATAATAAACTATTTGATTCA

GCGCCAATTTGCCCTTTTCCATTTTCCATTAAATCTCTGTTCTCTCTT

ACTTATATGATGATTAGGTATCATCTGTATAAAACTCCTTTCTTAATT

TCACTCTAAAGCATACCCCATAGAGAAGATCTTTCGGTTCGAAGACAT

TCCTACGCATAATAAGAATAGGAGGGAATAAttttcgagacc

For the 4 part assembly we used ADE13 CDS with the appropriate overhangs:

>ADE13_CDS
(SEQ ID NO: 33)
ggtctcaaATGCCTGACTATGACAATTACACTACGCCATTGTCTTCTA
GATATGCCTCCAAGGAAATGTCAGCAACGTTTTCTTTGAGAAACAGAT
TTTCCACATGGAGAAAACTATGGTTAAATTTGGCTATTGCTGAGAAGG
AATTGGGCTTAACTGTTGTTACAGATGAAGCAATTGAGCAAATGCGCA
AACACGTCGAAATCACTGATGATGAAATCGCAAAAGCTTCTGCTCAAG
AAGCCATTGTAAGACATGATGTTATGGCACATGTTCATACATTTGGTG
AAACTTGTCCGGCTGCTGCGGGTATCATTCACTTAGGTGCTACTTCCT
GTTTCGTTACAGACAATGCTGATCTAATCTTTATTAGGGACGCCTACG
ATATTATTATTCCAAAACTTGTTAACGTCATCAACAGATTGGCTAAGT
TTGCTATGGAATACAAGGATTTGCCTGTATTGGGTTGGACTCACTTTC
AACCAGCACAATTAACGACCTTGGGTAAGAGAGCTACTTTATGGATAC
AAGAGCTATTGTGGGATTTGAGAAACTTTGAAAGAGCTAGAAACGATA
TCGGTCTACGTGGTGTTAAGGGTACTACTGGTACTCAGGCATCATTCT
TGGCCTTATTCCATGGTAATCATGATAAAGTTGAAGCCCTTGACGAAA
GAGTAACTGAATTATTAGGTTTCGATAAGGTATATCCAGTCACTGGTC
AAACCTACTCAAGAAAAATTGACATTGACGTGTTGGCTCCTTTGTCTT
CTTTTGCTGCTACTGCACACAAAATGGCTACTGACATAAGATTATTAG
CCAACCTGAAGGAAGTTGAGGAACCTTTTGAGAAATCACAAATCGGAT
CCTCTGCTATGGCTTACAAGAGAAACCCAATGCGTTGTGAGAGAGTGT
GCTCCTTGGCTAGACACTTAGGTTCCTTGTTTAGTGACGCCGTTCAAA
CTGCATCCGTTCAATGGTTCGAAAGAACTCTGGATGATTCTGCTATTA
GAAGAATTTCTTTACCAAGTGCATTTTTAACCGCAGATATTCTATTAT
CTACTTTGTTGAACATCTCATCCGGTTTAGTTGTGTATCCAAAGGTTA
TCGAAAGGAGAATTAAGGGTGAACTACCTTTTATGGCTACTGAAAATA
TCATCATGGCTATGGTAGAAAAGAATGCCTCCAGACAAGAAGTACATG
AGCGTATTAGAGTGCTCTCTCATCAAGCCGCAGCAGTAGTCAAGGAAG
AAGGTGGGGAAAATGATTTAATTGAACGAGTAAAGAGGGATGAATTTT
TCAAGCCTATCTGGGAAGAATTAGATTCTTTACTGGAACCATCCACTT
TTGTTGGTAGAGCTCCACAACAAGTTGAGAAATTTGTTCAAAAAGACG
TTAACAATGCTTTACAACCTTTCCAAAAGTACCTAAACGATGAACAAG
TCAAGTTAAATGTTtgagcgagacctatgccgt For the 8 part assembly we used the FAS2 CDS that was cut into 5 parts with the appropriate overhangs:

>FAS2_CDS_Part1
(SEQ ID NO: 34)
ggtctcaaATGAAGCCGGAAGTTGAGCAAGAATTAGCTCATATTTTGC
TAACTGAATTGTTAGCTTATCAATTTGCCTCTCCTGTGAGATGGATTG
AAACTCAAGATGTTTTTTTGAAGGATTTTAACACTGAAAGGGTTGTTG
AAATCGGTCCTTCTCCAACTTTGGCTGGGATGGCTCAAAGAACCTTGA
AGAATAAATACGAATCTTACGATGCTGCTCTGTCTTTACATAGAGAAA
TCTTATGCTATTCGAAGGATGCCAAAGAGATTTATTATACCCCAGATC
CATCCGAACTAGCTGCAAAGGAAGAGCCCGCTAAGGAAGAAGCTCCTG
CTCCAACTCCAGCTGCTAGTGCTCCTGCTCCTGCAGCAGCAGCCCCAG
CTCCCGTCGCGGCAGCAGCCCCAGCTGCAGCAGCTGCTGAGATTGCCG
ATGAACCTGTCAAGGCTTCCCTATTGTTGCACGTTTTGGTTGCTCACA
AGTTGAAGAAGTCGTTAGATTCCATTCCAATGTCCAAGACAATCAAAG
ACTTGGTCGGTGGTAAATCTACAGTCCAAAATGAAATTTTGGGTGATT
TAGGTAAAGAATTTGGTACTACTCCTGAAAAACCAGAAGAAACTCCAT
TAGAAGAATTGGCAGAAACTTTCCAAGATACCTTCTCTGGAGCATTGG
GTAAGCAATCTTCCTCGTTATTATCAAGATTAATCTCATCTAAGATGC
CTGGTGGGTTTACTATTACTGTCGCTAGAAAATACTTACAAACTCGCT
GGGGACTACCATCTGGTAGACAAGATGGTGTCCTTTTGGTAGCTTTAT
CTAACGAGCCTGCTGCTCGTCTAGGTTCTGAAGCTGATGCCAAGGCTT
TCTTGGACTCCATGGCTCAAAAATACGCTTCCATTGTTGGTGTTGACT
TATCATCAGCTGCTAGCGCTAGTGGTGCTGCCGGTGCAGGTGCTGCTG
CCGGTGCAGCTATGATCGATGCTGGCGCTCTGGAAGAAATAACCAAAG
ACCACAAGGTTTTGGCGCGTCAACAACTGCAAGTATTGGCTCGTTATC
TAAAAATGGACTTGGATAACGGTGAAAGAAAGTTCTTGAAAGAAAAGG
ACACTGTTGCTGAACTTCAAGCTCAGTTGGATTACTTGAATGCCGAAT
TAGGTGAATTCtgagacc >FAS2_CDS_Part2
(SEQ ID NO: 35)
ggtctcaATTCTTTGTTAACGGTGTTGCTACTTCTTTCTCTAGAAAAA
AGGCCAGAACCTTCGATTCTTCCTGGAACTGGGCTAAACAATCTTTAT
TATCATTATACTTTGAGATAATTCATGGTGTCTTGAAAAACGTTGATA
GAGAGGTTGTTAGTGAAGCTATCAATATCATGAACAGATCTAACGATG
CTTTGATTAAATTCATGGAATACCATATCTCTAACACTGATGAAACAA
AAGGTGAAAACTATCAATTGGTTAAAACTCTTGGTGAGCAGTTGATTG
AAAACTGTAAACAAGTTTTGGATGTTGATCCAGTTTACAAAGATGTTG
CTAAGCCTACCGGTCCAAAAACTGCTATTGACAAGAACGGTAACATTA
CATACTCAGAAGAGCCAAGAGAAAAGGTTAGGAAATTATCTCAATACG
TACAAGAAATGGCCCTTGGTGGTCCAATCACCAAAGAATCTCAACCTA
CTATTGAAGAGGATTTGACTCGTGTTTACAAGGCAATCAGTGCTCAAG
CTGATAAACAAGATATTTCCAGCTCCACCAGGGTTGAATTTGAAAAAC
TATATAGTGATTTGATGAAGTTCTTGGAAAGCTCCAAAGAAATCGATC
CTTCTCAAACAACCCAATTGGCCGGTATGGATGTTGAGGATGCTTTGG
ACAAAGATTCCACCAAAGAAGTTGCTTCTTTGCCAAACAAATCTACCA
TTTCTAAGACGGTATCTTCAACTATTCCAAGAGAAACTATTCCGTTCT
TACATTTGAGAAAGAAGACTCCTGCCGGAGATTGGAAATATGACCGCC
AATTGTCTTCTCTTTTCTTAGATGGTTTAGAAAAGGCTGCCTTCAACG

```
GTGTCACCTTCAAGGACAAATACGTCTTGATCACTGGTGCTGGTAAGG

GTTCTATTGGTGCTGAAGTCTTGCAAGGTTTGTTACAAGGTGGTGCTA

AGGTTGTTGTTACCACCTCTCGTTTCTCTAAGCAAGTTACAGACTACT

ACCAATCCATTTACGCCAAATATGGTGCTAAGGGTTCTACTTTGATTG

TTGTTCCATTCAACCAAGGTTCTAAGCAAGACGTTGAAGCTTTGATTG

AATTTATCTACGACACTGAAAAGAATGGTGGTTTAGGTTGGGATCTAG

ATGCTATTATTCCATTCGCGGCCATTCCAGAACAAGGTATTGAATTAG

AACATATTGATTCTAAGTCTGAATTTGCTCATAGAATCATGTTGACCA

ATATCTTAAGAATGATGGGTTGTGTCAAGAAGCAAAAATCTGCAAGAG

GTATTGAAACAAGACCAGCTCAAGTCATTCTACCAATGTCTCCAAACC

ATGGTACTTTCGGTGGTGATGGTtgagacc

>FAS2_CDS_Part3
                                     (SEQ ID NO: 36)
ggtctcaTGGTATGTATTCAGAATCCAAGTTGTCTTTGGAAACTTTGT

TCAACAGATGGCACTCTGAATCCTGGGCCAATCAATTAACCGTTTGCG

GTGCTATTATTGGTTGGACTAGAGGTACTGGTTTAATGAGCGCTAATA

ACATCATTGCTGAAGGCATTGAAAAGATGGGTGTTCGTACTTTCTCTC

AAAAGGAAATGGCTTTCAACTTATTGGGTCTATTGACTCCAGAAGTCG

TAGAATTGTGCCAAAAATCACCTGTTATGGCTGACTTGAATGGTGGTT

TGCAATTTGTTCCTGAATTGAAGGAATTCACTGCTAAATTGCGTAAAG

AGTTGGTTGAAACTTCTGAAGTTAGAAAGGCAGTTTCCATCGAAACTG

CTTTGGAGCATAAGGTTGTCAATGGCAATAGCGCTGATGCTGCATATG

CTCAAGTCGAAATTCAACCAAGAGCTAACATTCAACTGGACTTCCCAG

AATTGAAACCATACAAACAGGTTAAACAAATTGCTCCCGCTGAGCTTG

AAGGTTTGTTGGATTTGGAAAGAGTTATTGTAGTTACCGGTTTTGCTG

AAGTCGGCCCATGGGGTTCGGCCAGAACAAGATGGGAAATGGAAGCTT

TTGGTGAATTTTCGTTGGAAGGTTGCGTTGAAATGGCCTGGATTATGG

GCTTCATTTCATACCATAACGGTAATTTGAAGGGTCGTCCATACACTG

GTTGGGTTGATTCCAAAACAAAAGAACCAGTTGATGACAAGGACGTTA

AGGCCAAGTATGAAACATCAATCCTAGAACACAGTGGTATCAGATTGA

TCGAACCAGAGTTATTCAATGGTTACAACCCAGAAAAGAAGGAAATGA

TTCAAGAAGTCATTGTCGAAGAAGACTTGGAACCATTTGAGGCTTCGA

AGGAAACTGCCGAACAATTTAAACACCAACATGGTGACAAAGTGGATA

TCTTCGAAATCCCAGAAACAGGAGAGTACTCTGTTAAGTTACTAAAGG

GTGCCACTTTATACATTCCAAAGGCTTTGAGATTTGACCGTTTGGTTG

CAGGTCAAATTCCAACTGGTTGGAATGCTAAGACTTATGGTATCTCTG

ATGATATCATTTCTCAGGTTGACCCAATCACATTATTCGTTCTCGTCT

CTGTTGtgagacc

>FAS2_CDS_Part4
                                     (SEQ ID NO: 37)
GGTCTCTGTTGTGGAAGCATTTATTGCATCTGGTATCACCGACCCATA

CGAAATGTACAAATACGTACATGTTTCTGAGGTTGGTAACTGTTCTGG

TTCTGGTATGGGTGGTGTTTCTGCCTTACGTGGTATGTTTAAGGACCG

TTTCAAGGATGAGCCTGTCCAAAATGATATTTTACAAGAATCATTTAT

CAACACCATGTCCGCTTGGGTTAATATGTTGTTGATTTCCTCATCTGG

TCCAATCAAGACACCTGTTGGTGCCTGTGCCACATCCGTGGAATCTGT

TGACATTGGTGTAGAAACCATCTTGTCTGGTAAGGCTAGAATCTGTAT

TGTCGGTGGTTACGATGATTTCCAAGAAGAAGGCTCCTTTGAGTTCGG

TAACATGAAGGCCACTTCCAACACTTTGGAAGAATTTGAACATGGTCG

TACCCCAGCGGAAATGTCCAGACCTGCCACCACTACCCGTAACGGTTT

TATGGAAGCTCAAGGTGCTGGTATTCAAATCATCATGCAAGCTGATTT

AGCTTTGAAGATGGGTGTGCCAATTTACGGTATTGTTGCCATGGCTGC

TACCGCCACCGATAAGATTGGTAGATCTGTGCCAGCTCCAGGTAAGGG

TATTTTAACCACTGCTCGTGAACACCACTCCAGTGTTAAGTATGCTTC

ACCAAACTTGAACATGAAGTACAGAAAGCGCCAATTGGTTACTCGTGA

AGCTCAGATTAAAGATTGGGTAGAAAACGAATTGGAAGCTTTGAAGTT

GGAGGCCGAAGAAATTCCAAGCGAAGACCAAAACGAGTTCTTACTTGA

ACGTACCAGAGAAATCCACAACGAAGCTGAAAGTCAATTGAGAGCTGC

ACAACAACAATGGGGTAACGACTTCTACAAGAGGGACCCACGTATTGC

TCCATTGAGAGGAGCACTGGCTACTTACGGTTTAACTATTGATGACTT

GGGTGTCGCTTCATTCCACGGtgagacc

>FAS2_CDS_Part5
                                     (SEQ ID NO: 38)
ggtctcaACGGTACATCCACAAAGGCTAATGACAAGAACGAATCTGCC

ACAATTAATGAAATGATGAAGCATTTGGGTAGATCTGAAGGTAATCCC

GTCATTGGTGTTTTCCAAAAGTTCTTGACTGGTCATCCAAAGGGTGCT

GCTGGTGCATGGATGATGAATGGTGCTTTGCAAATTCTAAACAGTGGT

ATTATTCCAGGTAACCGTAACGCTGATAACGTGGATAAGATCTTGGAG

CAATTTGAATACGTCTTGTACCCATCCAAGACTTTAAAGACCGACGGT

GTCAGAGCCGTGTCCATCACTTCTTTCGGTTTTGGTCAAAAGGGTGGT

CAAGCTATTGTGGTTCATCCAGACTACTTATACGGTGCTATCACTGAA

GACAGATACAACGAGTATGTCGCCAAGGTTAGTGCCAGAGAGAAAAGT

GCCTACAAATTCTTCCATAATGGTATGATCTACAACAAGTTGTTCGTA

AGTAAAGAGCATGCTCCATACACTGATGAATTGGAAGAGGATGTTTAC

TTGGACCCATTAGCCCGTGTATCTAAGGATAAGAAATCAGGCTCCTTG

ACTTTCAACTCTAAAAACATCCAAAGCAAGGACAGTTACATCAATGCT

AACACCATTGAAACTGCCAAGATGATTGAAAACATGACCAAGGAGAAA

GTCTCTAACGGTGGCGTCGGTGTAGATGTTGAATTAATCACTAGCATC

AACGTTGAAAATGATACTTTTATCGAGCGCAATTTCACCCCGCAAGAA

ATAGAGTACTGCAGCGCGCAGCCTAGTGTGCAAAGCTCTTTCGCTGGG

ACATGGTCCGCCAAAGAGGCTGTTTTCAAGTCCTTAGGCGTCAAGTCC

TTAGGCGGTGGTGCTGCATTGAAAGACATCGAAATCGTACGCGTTAAC

AAAAACGCTCCAGCCGTTGAACTGCACGGTAACGCCAAAAAGGCTGCC
```

```
GAAGAAGCTGGTGTTACCGATGTGAAGGTATCTATTTCTCACGATGAC

CTCCAAGCTGTCGCGGTCGCCGTTTCTACTAAGAAAtgagcgagacct atgccgt
```

For C-terminal tagging we used pAV115 as acceptor vector (Table 2) and the following parts (BceAI site is marked in green):

```
>HPT1p
                                           (SEQ ID NO: 39)
ggtctcacagtTCGTTTATCCTTTTTGAACTGCATCTGGCATCGTTAA

CAGTAAGGCCATCTGGAACATCAAGCAAGCACTCCACTTTTACGTCAC

AACCATAGTTGGTTAACTAAGAAAAGACAGTACATATTTCCCTTCCGA

GTCACTTATTTTTTTTTCTTCTGAAAAAATTAATTAGATTAATTTCA

ATTAATATCATTTCCGCTTATCTGACTTCTTTCATTTTTTTTCTCTAT

ATTTCGCGTTTACTAGGAAAGAAAAGGAAAAAAAATTTTTCCCCCTCC

ATCTGTCCCAAATCGGGTAGCGATGAGCTGCTATAGAATTTTCTATTT

AAACATGTTTGATAAGCCCAATTTCCGTTAGATTTTGTTCCCCCTTCG

CAGTTTGGTTTGCCGTAACTTTTTTATTTTAGTCTCCATCTAGCTGGA

GTAATACGATGTAGTGCCTTGTAATCTTTCTTATTTTTATATTACCGT

TCGTGTTCATTATATCCATTACGTTCCCATAaatgcgagacc

>HPT1t
                                           (SEQ ID NO: 40)
ggtctcatgagTAGACATATCATATCCTTCAGTAACTTGAATCATACA

GCAGAATTTGTACAATAGACAACGCATATAACTGCGACCATATGTATA

CGTATAACTAATTATTATCTCAAAGTTTATTCCCTTAGCCTCACCGGT

AACCTGTGAGGCGCGATTACGTTTTCCCTCTGTTCACCACCACGTAAC

GCGATATTTGACACATACGttttcgagacc

>HPT1_CDS
                                           (SEQ ID NO: 41)
ggtctcaaATGTCGGCAAACGATAAGCAATACATCTCGTACAACAACG

TACATCAACTATGTCAAGTATCCGCTGAGAGAATTAAGAATTTCAAGC

CGGACTTAATCATTGCCATTGGTGGTGGTGGTTTCATTCCTGCTAGGA

TCCTACGTACGTTCCTAAAGGAGCCCGGCGTGCCAACCATCAGAATTT

TTGCTATTATTTTGTCTTTGTACGAAGATTTGAACAGTGTAGGCTCAG

AAGTTGAGGAAGTTGGTGTTAAGGTTAGCAGAACACAATGGATTGATT

ACGAGCAATGTAAATTAGATCTAGTCGGCAAGAACGTTCTTATCGTTG

ACGAAGTCGATGACACCCGTACCACACTTCATTACGCTTTGAGTGAAT

TGGAAAAGGATGCAGCTGAACAGGCAAAGGCTAAAGGTATCGATACTG

AAAAGTCTCCAGAGATGAAAACAAACTTCGGGATTTTTGTTCTACACG

ATAAGCAAAAACCAAAGAAAGCAGATTTGCCTGCCGAAATGTTGAATG

ACAAGAACCGTTATTTTGCAGCTAAAACTGTTCCAGACAAGTGGTATG

CATATCCATGGGAATCTACTGACATTGTTTTCCATACTAGAATGGCTA
```

```
TTGAACAGGGCAATGACATCTTTATTCCTGAGCAGGAACACAAGCAAt gagcgagacctatgccgt

>GFP_tag
                                           (SEQ ID NO: 42)
ggtctcaggatcaATGGTGAGCAAGGGCGAGGAGCTGTTCACCGGGGT

GGTGCCCATCCTGGTCGAGCTGGACGGCGACGTAAACGGCCACAAGTT

CAGCGTGAGGGGCGAAGGCGAGGGCGATGCCACCAACGGCAAGCTGAC

CCTGAAGTTCATCTGCACCACCGGCAAGCTGCCCGTGCCCTGGCCCAC

CCTCGTGACCACCTTGACCTACGGCGTGCAGTGCTTCGCCCGCTACCC

CGACCACATGAAGCAGCACGACTTCTTCAAGTCCGCCATGCCCGAAGG

CTACGTCCAGGAGCGCACCATCTTCTTCAAGGACGACGGCACCTACAA

GACCCGCGCCGAGGTGAAGTTCGAGGGCGACACCCTGGTGAACCGCAT

CGAGCTGAAGGGCATCGACTTCAAGGAGGACGGCAACATCCTGGGGCA

CAAGCTGGAGTACAACTACAACAGCCACAAGGTCTATATCACCGCCGA

CAAGCAGAAGAACGGCATCAAGGTGAACTTCAAGATCCGCCACAACGT

GGAGGACGGCAGCGTGCAGCTCGCCGACCACTACCAGCAGAACACCCC

CATCGGCGACGGCCCCGTGCTGCTGCCCGACAACCACTACCTGAGCAC

CCAGTCCGTGCTGAGCAAAGACCCCAACGAGAAGCGCGATCACATGGT

CCTGCTGGAGTTCGTGACCGCCGCCGGGATCACTCTCGGCATGGACGA

GCTGTACAAGTAAtgagcgagacc

>mCherry_tag
                                           (SEQ ID NO: 43)
ggtctcaggatcaATGGTGAGCAAGGGCGAGGAGGATAACATGGCCAT

CATCAAGGAGTTCATGCGCTTCAAGGTGCACATGGAGGGCTCCGTGAA

CGGCCACGAGTTCGAGATCGAGGGCGAGGGCGAGGGCCGCCCCTACGA

GGGCACCCAGACCGCCAAGCTGAAGGTGACCAAGGGTGGCCCCCTGCC

CTTCGCCTGGGACATCCTGTCCCCTCAGTTCATGTACGGCTCCAAGGC

CTACGTGAAGCACCCCGCCGACATCCCCGACTACTTGAAGCTGTCCTT

CCCCGAGGGCTTCAAGTGGGAGCGCGTGATGAACTTCGAGGACGGCGG

CGTGGTGACCGTGACCCAGGACTCCTCCCTGCAGGACGGCGAGTTCAT

CTACAAGGTGAAGCTGCGCGGCACCAACTTCCCCTCCGACGGCCCCGT

AATGCAGAAGAAGACCATGGGCTGGGAGGCCTCCTCCGAGCGGATGTA

CCCCGAGGACGGCGCCCTGAAGGGCGAGATCAAGCAGAGGCTGAAGCT

GAAGGACGGCGGCCACTACGACGCTGAGGTCAAGACCACCTACAAGGC

CAAGAAGCCCGTGCAGCTGCCCGGCGCCTACAACGTCAACATCAAGTT

GGACATCACCTCCCACAACGAGGACTACACCATCGTGGAACAGTACGA

ACGCGCCGAGGGCCGCCACTCCACCGGCGGCATGGACGAGCTGTACAA

GTAAtgagcgagacc
```

For the V5 tag two oligos were ordered and annealed:

V5 oligo 1:
(SEQ ID NO: 44)
5' tgtGGTAAGCCTATCCCTAACCCTCTCCTCGGACTCGATTCTACG

V5 oligo 2:
(SEQ ID NO: 45)
5' taggCGTAGAATCGAGTCCGAGGAGAGGGTTAGGGATAGGCTTACCa

The foregoing Examples are intended to illustrate but not limit various aspects of the disclosure.

What is claimed is:

1. A method for making recombinant vectors suitable for homologous recombination with each other in yeast comprising:
   i) providing a first recombinant vector (CDS vector) comprising a protein coding sequence (CDS sequence) wherein the CDS is flanked on its 5' and 3' ends by first Type IIS restriction enzyme recognition sites, the CDS vector further comprising a first antibiotic resistance gene;
   ii) providing a second recombinant vector (PRO vector) comprising a promoter sequence (PRO sequence) wherein the PRO sequence is flanked on its 5' and 3' ends by the first Type IIS restriction enzyme recognition sites, the PRO vector further comprising the first antibiotic resistance gene;
   iii) providing a third recombinant vector (TER vector) comprising a transcription termination sequence (TER sequence) wherein the TER sequence is flanked on its 5' and 3' ends by the first restriction Type IIS enzyme recognition sites, the TER vector further comprising the first antibiotic resistance gene;
   iv) providing a fourth recombinant vector (LVA vector) comprising a first left adapter polynucleotide sequence (LVA sequence) wherein the LVA sequence is flanked on its 5' and 3' ends by the first Type IIS restriction enzyme recognition sites, the LVA vector further comprising the first antibiotic resistance gene;
   v) providing a fifth recombinant vector (RVA vector) comprising a first right adapter polynucleotide sequence (RVA sequence) wherein the RVA sequence is flanked on its 5' and 3' ends by the first Type IIS restriction enzyme recognition sites, the RVA vector further comprising the first antibiotic resistance gene; wherein the LVA sequence comprises the sequence:

(SEQ ID NO: 1)
   CCCCTTAGGTTGCAAATGCTCCGTCGACGGGATCTGTCCTTCTCTGCCGGC

GATCGT (VA1*), and/or wherein the RVA sequence comprises the sequence:

(SEQ ID NO: 2)
   TGACGCTTGGATGCGTGACCCCGTACGTCATGACCCGTCATGGGTATGTAA

GCGAAG (VA2**);

vi) providing a sixth recombinant vector (acceptor vector) comprising a segment, the segment comprising a polynucleotide sequence encoding a detectable marker (detectable marker sequence), wherein the detectable marker sequence is flanked by the first Type IIS restriction enzyme recognition sites, and wherein the segment is flanked by a second Type IIS restriction enzyme recognition sites, wherein the acceptor vector comprises a second antibiotic resistance gene but does not comprise the first antibiotic resistance gene;
   vii) incubating the CDS vector, the PRO vector, the TER vector, the LVA vector, the RVA vector, and the acceptor vector in a single reaction container with a first Type IIS restriction endonuclease that recognizes the first Type IIS restriction endonuclease recognition site and a DNA ligase enzyme such that ligated vectors are produced, wherein the ligated vectors comprise sequentially the LVA sequence, the PRO sequence, the CDS sequence, the TER sequence, and the RVA sequence (LVA-TU-RVA vectors), wherein the PRO, CDS and TER sequences comprise a transcription unit (TU), and wherein the LVA-TU-RVA vectors comprise the second antibiotic resistance gene, but do not comprise the first antibiotic resistance gene, wherein the LVA-TU-RVA vectors do not comprise the detectable marker sequence, and wherein the ligated vectors do not comprise the first Type IIS restriction site, but do comprise the second Type IIS restriction site;
   viii) introducing the LVA-TU-RVA vectors from vii) into bacteria and culturing the bacteria with a culture medium comprising an antibiotic to which bacteria comprising the LVA-TU-RVA vectors are resistant via expression of the second antibiotic resistance gene such that clonal colonies of the bacteria comprising the VEGAS vectors are formed, wherein the clonal colonies do not express the detectable marker; and
   viii) isolating the LVA-TU-RVA vectors from the colonies that do not express the detectable marker to obtain isolated LVA-TU-RVA vectors.

2. The method of claim 1, wherein in steps i)-vi):
   a) the CDS sequence comprises on its 5' end the sequence: AATG and at its 3' end the sequence TGAG; and
   b) the PRO sequence comprises at its 5' end the sequence: CAGT and at its 3' end the sequence AATG; and
   c) the TER sequence comprises at its 5' end the sequence TGAG and at its 3' end the sequence TTTT; and
   d) the LVA sequence comprises at its 5' end the sequence CCTG and at its 3' end the sequence CAGT; and;
   e) the RVA sequence comprises at its 5' end TTTT and at its 3' end the sequence AACT; and
   f) the detectable marker sequence comprises at its 5' end the sequence CCTG and at its 3' end the sequence AACT.

3. A method for producing a homologously recombined DNA molecule comprising distinct transcription units (TU) of claim 1, the method comprising:
   i) providing a plurality of LVA-TU-RVA vectors obtained using the method of claim 1, wherein each LVA-TU-RVA vector in the plurality comprises a distinct TU that comprises a distinct coding sequence (CDS), and wherein each LVA-TU-RVA vector further comprises a left adapter polynucleotide sequence (LVA sequence) and a right adapter polynucleotide sequence (RVA sequence), wherein only one LVA-TU-RVA vector in the plurality comprises a first LVA sequence (VA1 sequence) that is identical to a first LVA sequence in a yeast VEGAS acceptor vector, and wherein only one LVA-TU-RVA vector in the plurality comprises a first RVA sequence (VA2 sequence) that is identical to a first RVA sequence in the yeast VEGAS acceptor vector;

ii) linearizing the plurality of LVA-TU-RVA vectors by digestion with a Type IIS restriction enzyme that recognizes the second Type IIS restriction site of claim 1 to obtain distinct linearized LVA-TU-RVA vector fragments that comprise the distinct TUs;

iii) providing a linearized yeast VEGAS acceptor vector that comprises at one end the VA1 sequence and at the other end the VA2 sequence, the linearized yeast VEGAS acceptor vector further comprising a sequence encoding selectable marker functional in bacteria, a selectable marker functional in yeast, a yeast centromere (CEN) sequence, and a yeast autonomously replicating sequences (ARS);

iv) introducing into the yeast the linearized yeast VEGAS acceptor vector and the distinct linearized LVA-TU-RVA vector fragments that comprise the distinct TUs;

v) allowing homologous recombination in the yeast so that the only one LVA-TU-RVA vector segment comprising the VA1 sequence and the only one LVA-TU-RVA vector segment comprising the VA2 sequence are homologously recombined with the linearized yeast VEGAS acceptor vector to form circularized double stranded DNA polynucleotides comprising at least the two distinct TUs, and optionally, vi) isolating the circularized double stranded DNA polynucleotides from the yeast.

4. The method of claim 3, wherein in i) the plurality of LVA-TU-RVA vectors comprises at least one, two, three or four additional distinct LVA-TU-RVA vectors.

5. The method of claim 3, wherein the plurality of LVA-TU-RVA vectors comprises one, two, three or four additional distinct LVA-TU-RVA vectors, wherein each of the additional LVA-TU-RVA vectors comprises an LVA sequence and an RVA sequence selected from the group consisting of:

VA1*
(SEQ ID NO: 1)
CCCCTTAGGTTGCAAATGCTCCGTCGACGGGATCTGTCCTTCTCTGCCGGC
GATCGT;

VA2**
(SEQ ID NO: 2)
TGACGCTTGGATGCGTGACCCCGTACGTCATGACCCGTCATGGGTATGTAA
GCGAAG;

VA3
(SEQ ID NO: 16)
GGAGGTACTGGCCTAGCGTCGTGGCCCGGGAGAGACAGTTTAGTAGTGACT
CGCGGC;

VA4
(SEQ ID NO: 17)
TTGGCGTTAATTGTAGCTTATTTCCCGCCCTGTGATTGAGGCGGGATGGTG
TCCCCA;

VA5
(SEQ ID NO: 18)
GACTAAGACTCTGGTCACGGTTCAGAAGTGGACGATGCATGTCGTCGGGCT
GATAGA;

VA6
(SEQ ID NO: 19)
TGCACGGCGCTAGGTGTGATATCGTACACTTGGGAGAAGTCAGATACGATT
GCGGCT;

VA7
(SEQ ID NO: 20)
TAGCGGCGCCGGGAAATCCAGCATATTCTCGCGGCCCTGAGCAGTAGGTGT
CTCGGG;

VA8
(SEQ ID NO: 21)
GAGTCTACGTTACACCTGAACTCGCATGTCTGGGGTTGTGGTCAGGCCTTG
TCAATT;

VA9
(SEQ ID NO: 22)
GCGTACTGGCCGCCCGGGCCTGATGTGGCCGTCCTATTAGCATTGTACACC
CTCATT;

VA10
(SEQ ID NO: 23)
CTTGAATCGGCTTTAGGATCCGGTACTGCCGACGCACTTTAGAACGGCCAC
CGTCCT;

VA11
(SEQ ID NO: 24)
GCAAGTTTTGAAGAGGTGTAAACTCTCCGCAGCACCTCCGGACTATGCCCG
AGTGGT;

VA12
(SEQ ID NO: 25)
TGAAGCTACGCGCCGAGCGTCTGACTCCTTTAGTCCGCGTCATCGCTTTGA
GCGCGT;

VA13
(SEQ ID NO: 26)
TCCGGATCCCTTTCGGTCCATATAGCGGATTTCCATAGACGTAGACCGCGC
CAATGT;

VA14
(SEQ ID NO: 27)
GACGACGCGTTCTGTGTCTTCGTTGCGGCTCTGCGCTTGGTCGTTGGCGAC
GGCCGT;

VA15
(SEQ ID NO: 28)
TGTAAGGGCGTCTGTTAACCCAAGGTCCCTCGAACCGTATGCAGAGCCGTG
GCTACG;

VA16
(SEQ ID NO: 29)
TATCGCGGGTGCGTGCATCGACAAGCCATGCCCACCTTCTGGTCGATTGGG
CTGGCG;

VA17
(SEQ ID NO: 30)
CATCCATCGATATTTGGCACTGGACCTCAACGCTAGTGTTCGCGGACTGCA
CTACCT;

VA18;
(SEQ ID NO: 31)
GATTAAGGGGCATACCGTGCCTATCCTGGTAATTGTGTAGGCTACCTGTCT
GTATAC;

and combinations thereof.

6. Yeast cells comprising a homologously recombined DNA molecule made by the process of claim 3.

7. The yeast cells of claim 6, wherein the homologously recombined DNA molecule comprises at least one, two, three or four additional distinct transcription units (TUs), wherein each TU encodes a distinct polypeptide that is not endogenous to the yeast cells.

8. The yeast cells of claim 7, wherein the distinct polypeptides are components of a biosynthetic pathway.

9. Homologously recombined DNA molecules isolated from the yeast cells of claim 6.

10. The homologously recombined DNA molecules of claim 9 comprising more than two distinct TUs.

11. The homologously recombined DNA molecules of claim 9 comprising at least six distinct TUs.

\* \* \* \* \*

```
                           SEQUENCE LISTING

<160> NUMBER OF SEQ ID NOS: 54

<210> SEQ ID NO 1
<211> LENGTH: 57
<212> TYPE: DNA
<213> ORGANISM: artificial sequence
<220> FEATURE:
<223> OTHER INFORMATION: Yeast nonhomologous sequence

<400> SEQUENCE: 1
ccccttaggt tgcaaatgct ccgtcgacgg gatctgtcct tctctgccgg cgatcgt       57

<210> SEQ ID NO 2
<211> LENGTH: 57
<212> TYPE: DNA
<213> ORGANISM: artificial sequence
<220> FEATURE:
<223> OTHER INFORMATION: East nonhomologous sequence

<400> SEQUENCE: 2
tgacgcttgg atgcgtgacc ccgtacgtca tgacccgtca tgggtatgta agcgaag       57

<210> SEQ ID NO 3
<211> LENGTH: 19
<212> TYPE: DNA
<213> ORGANISM: artificial sequence
<220> FEATURE:
<223> OTHER INFORMATION: Synthetic sequence

<400> SEQUENCE: 3
acggcatagg tctcgctca                                                 19

<210> SEQ ID NO 4
<211> LENGTH: 11
<212> TYPE: DNA
<213> ORGANISM: artificial sequence
<220> FEATURE:
<223> OTHER INFORMATION: Type II restriction enzyme recognition sequence

<400> SEQUENCE: 4
ggtctcacag t                                                         11

<210> SEQ ID NO 5
<211> LENGTH: 11
<212> TYPE: DNA
<213> ORGANISM: artificial sequence
<220> FEATURE:
<223> OTHER INFORMATION: Restriction digest site

<400> SEQUENCE: 5
aatgcgagac c                                                         11

<210> SEQ ID NO 6
<211> LENGTH: 11
<212> TYPE: DNA
<213> ORGANISM: artificial sequence
<220> FEATURE:
<223> OTHER INFORMATION: Restriction site
```

```
<400> SEQUENCE: 6
cgtctcacag t                                                        11

<210> SEQ ID NO 7
<211> LENGTH: 11
<212> TYPE: DNA
<213> ORGANISM: artificial sequence
<220> FEATURE:
<223> OTHER INFORMATION: Restriction site

<400> SEQUENCE: 7
aatgcgagac g                                                        11

<210> SEQ ID NO 8
<211> LENGTH: 11
<212> TYPE: DNA
<213> ORGANISM: artificial sequence
<220> FEATURE:
<223> OTHER INFORMATION: Restriction site

<400> SEQUENCE: 8
ggtctcaaat g                                                        11

<210> SEQ ID NO 9
<211> LENGTH: 11
<212> TYPE: DNA
<213> ORGANISM: artificial sequence
<220> FEATURE:
<223> OTHER INFORMATION: Restriction site

<400> SEQUENCE: 9
tgagcgagac c                                                        11

<210> SEQ ID NO 10
<211> LENGTH: 11
<212> TYPE: DNA
<213> ORGANISM: artificial sequence
<220> FEATURE:
<223> OTHER INFORMATION: Restriction site

<400> SEQUENCE: 10
cgtctcaaat g                                                        11

<210> SEQ ID NO 11
<211> LENGTH: 11
<212> TYPE: DNA
<213> ORGANISM: artificial sequence
<220> FEATURE:
<223> OTHER INFORMATION: Restriction site

<400> SEQUENCE: 11
tgagcgagac g                                                        11

<210> SEQ ID NO 12
<211> LENGTH: 11
<212> TYPE: DNA
<213> ORGANISM: artificial sequence
<220> FEATURE:
<223> OTHER INFORMATION: Restriction site

<400> SEQUENCE: 12
ggtctcatga g                                                        11

<210> SEQ ID NO 13
```

```
<211> LENGTH: 11
<212> TYPE: DNA
<213> ORGANISM: artificial sequence
<220> FEATURE:
<223> OTHER INFORMATION: Restriction site

<400> SEQUENCE: 13
ttttcgagac c                                                            11

<210> SEQ ID NO 14
<211> LENGTH: 11
<212> TYPE: DNA
<213> ORGANISM: artificial sequence
<220> FEATURE:
<223> OTHER INFORMATION: Restriction site

<400> SEQUENCE: 14
cgtctcatga g                                                            11

<210> SEQ ID NO 15
<211> LENGTH: 11
<212> TYPE: DNA
<213> ORGANISM: artificial sequence
<220> FEATURE:
<223> OTHER INFORMATION: Restriction site

<400> SEQUENCE: 15
ttttcgagac g                                                            11

<210> SEQ ID NO 16
<211> LENGTH: 57
<212> TYPE: DNA
<213> ORGANISM: artificial sequence
<220> FEATURE:
<223> OTHER INFORMATION: Yeast nonhomologous sequence

<400> SEQUENCE: 16
ggaggtactg gcctagcgtc gtggcccggg agagacagtt tagtagtgac tcgcggc         57

<210> SEQ ID NO 17
<211> LENGTH: 57
<212> TYPE: DNA
<213> ORGANISM: artificial sequence
<220> FEATURE:
<223> OTHER INFORMATION: Yeast nonhomologous sequence

<400> SEQUENCE: 17
ttggcgttaa ttgtagctta tttcccgccc tgtgattgag gcgggatggt gtccca          57

<210> SEQ ID NO 18
<211> LENGTH: 57
<212> TYPE: DNA
<213> ORGANISM: artificial sequence
<220> FEATURE:
<223> OTHER INFORMATION: yeast nonhomologous sequence

<400> SEQUENCE: 18
gactaagact ctggtcacgg ttcagaagtg gacgatgcat gtcgtcgggc tgataga        57

<210> SEQ ID NO 19
<211> LENGTH: 57
<212> TYPE: DNA
<213> ORGANISM: artificial sequence
<220> FEATURE:
<223> OTHER INFORMATION: Yeast nonhomologous sequence

<400> SEQUENCE: 19
```
tgcacggcgc taggtgtgat atcgtacact tgggagaagt cagatacgat tgcggct      57

<210> SEQ ID NO 20
<211> LENGTH: 57
<212> TYPE: DNA
<213> ORGANISM: artificial sequence
<220> FEATURE:
<223> OTHER INFORMATION: Yeast nonhomologous sequence

<400> SEQUENCE: 20
tagcggcgcc gggaaatcca gcatattctc gcggccctga gcagtaggtg tctcggg      57

<210> SEQ ID NO 21
<211> LENGTH: 57
<212> TYPE: DNA
<213> ORGANISM: artificial sequence
<220> FEATURE:
<223> OTHER INFORMATION: Yeast nonhomologous sequence

<400> SEQUENCE: 21
gagtctacgt tacacctgaa ctcgcatgtc tggggttgtg gtcaggcctt gtcaatt      57

<210> SEQ ID NO 22
<211> LENGTH: 57
<212> TYPE: DNA
<213> ORGANISM: artificial sequence
<220> FEATURE:
<223> OTHER INFORMATION: Yeast nonhomologous sequence

<400> SEQUENCE: 22
gcgtactggc cgcccgggcc tgatgtggcc gtcctattag cattgtacac cctcatt      57

<210> SEQ ID NO 23
<211> LENGTH: 57
<212> TYPE: DNA
<213> ORGANISM: artificial sequence
<220> FEATURE:
<223> OTHER INFORMATION: Yeast nonhomologous sequence

<400> SEQUENCE: 23
cttgaatcgg ctttaggatc cggtactgcc gacgcacttt agaacggcca ccgtcct      57

<210> SEQ ID NO 24
<211> LENGTH: 57
<212> TYPE: DNA
<213> ORGANISM: artificial sequence
<220> FEATURE:
<223> OTHER INFORMATION: Yeast nonhomologous sequence

<400> SEQUENCE: 24
gcaagttttg aagaggtgta aactctccgc agcacctccg gactatgccc gagtggt      57

<210> SEQ ID NO 25
<211> LENGTH: 57
<212> TYPE: DNA
<213> ORGANISM: artificial sequence
<220> FEATURE:
<223> OTHER INFORMATION: Yeast nonhomologous sequence

<400> SEQUENCE: 25
tgaagctacg cgccgagcgt ctgactcctt tagtccgcgt catcgctttg agcgcgt      57

<210> SEQ ID NO 26
<211> LENGTH: 57
<212> TYPE: DNA

<213> ORGANISM: artificial sequence
<220> FEATURE:
<223> OTHER INFORMATION: Yeast nonhomologous sequence

<400> SEQUENCE: 26
tccggatccc tttcggtcca tatagcggat ttccatagac gtagaccgcg ccaatgt  57

<210> SEQ ID NO 27
<211> LENGTH: 57
<212> TYPE: DNA
<213> ORGANISM: artificial sequence
<220> FEATURE:
<223> OTHER INFORMATION: Yeast nonhomologous sequence

<400> SEQUENCE: 27
gacgacgcgt tctgtgtctt cgttgcggct ctgcgcttgg tcgttggcga cggccgt  57

<210> SEQ ID NO 28
<211> LENGTH: 57
<212> TYPE: DNA
<213> ORGANISM: artificial sequence
<220> FEATURE:
<223> OTHER INFORMATION: Yeast nonhomologous sequence

<400> SEQUENCE: 28
tgtaagggcg tctgttaacc caaggtccct cgaaccgtat gcagagccgt ggctacg  57

<210> SEQ ID NO 29
<211> LENGTH: 57
<212> TYPE: DNA
<213> ORGANISM: artificial sequence
<220> FEATURE:
<223> OTHER INFORMATION: Yeast nonhomologous sequence

<400> SEQUENCE: 29
tatcgcgggt gcgtgcatcg acaagccatg cccaccttct ggtcgattgg gctggcg  57

<210> SEQ ID NO 30
<211> LENGTH: 57
<212> TYPE: DNA
<213> ORGANISM: artificial sequence
<220> FEATURE:
<223> OTHER INFORMATION: Yeast nonhomologous sequence

<400> SEQUENCE: 30
catccatcga tatttggcac tggacctcaa cgctagtgtt cgcggactgc actacct  57

<210> SEQ ID NO 31
<211> LENGTH: 57
<212> TYPE: DNA
<213> ORGANISM: artificial sequence
<220> FEATURE:
<223> OTHER INFORMATION: Yeast nonhomologous sequence

<400> SEQUENCE: 31
gattaagggg cataccgtgc ctatcctggt aattgtgtag gctacctgtc tgtatac  57

<210> SEQ ID NO 32
<211> LENGTH: 522
<212> TYPE: DNA
<213> ORGANISM: artificial sequence
<220> FEATURE:
<223> OTHER INFORMATION: Promoter

<400> SEQUENCE: 32
ggtctcacag ttggaacttt cagtaatacg cttaactgct cattgctata ttgaagtacg  60

-continued

```
gattagaagc cgccgagcgg gcgacagccc tccgacggaa gactctcctc cgtgcgtcct        120
cgtcttcacc ggtcgcgttc ctgaaacgca gatgtgcctc gcgccgcact gctccgaaca        180
ataaagattc tacaatacta gcttttatgg ttatgaagag gaaaaattgg cagtaacctg        240
gccccacaaa ccttcaaatt aacgaatcaa attaacaacc ataggatgat aatgcgatta        300
gttttttagc cttatttctg ggtaattaa tcagcgaagc gatgattttt gatctattaa         360
cagatatata aatggaaaag ctgcataacc actttaacta atactttcaa cattttcagt        420
ttgtattact tcttattcaa atgtcataaa agtatcaaca aaaaattgtt aatatacctc        480
tatactttaa cgtcaaggag aaaaaactat aaatgcgaga cc                          522
```

<210> SEQ ID NO 33
<211> LENGTH: 858
<212> TYPE: DNA
<213> ORGANISM: artificial sequence
<220> FEATURE:
<223> OTHER INFORMATION: Promoter

<400> SEQUENCE: 33

```
ggtctcatga ggtatacttc tttttttttac tttgttcaga acaacttctc atttttttct        60
actcataact ttagcatcac aaaatacgca ataataacga gtagtaacac ttttatagtt       120
catacatgct tcaactactt aataaatgat tgtatgataa tgttttcaat gtaagagatt       180
tcgattatcc acaaacttta aaacacaggg acaaaattct tgatatgctt tcaaccgctg       240
cgttttggat acctattctt gacatgatat gactaccatt ttgttattgt acgtggggca       300
gttgacgtct tatcatatgt caaagtcatt tgcgaagttc ttggcaagtt gccaactgac       360
gagatgcagt aaaagagat tgccgtcttg aaacttttg tcctttttt tttccgggga         420 ctctacgaga acccttgtc ctactgatta attttgtact gaatttggac aattcagatt        480
ttagtagaca agcgcgagga ggaaaagaaa tgacagaaaa attccgatgg acaagaagat       540
aggaaaaaaa aaaagctttc accgatttcc tagaccggaa aaagtcgta tgacatcaga       600 atgaaaaatt ttcaagttag acaaggacaa atcaggaca aattgtaaag atataataaa      660
ctatttgatt cagcgccaat ttgccctttt ccattttcca ttaaatctct gttctctctt       720
acttatatga tgattaggta tcatctgtat aaaactcctt tcttaatttc actctaaagc      780
ataccccata gagaagatct ttcggttcga agacattcct acgcataata agaataggag      840
ggaataattt tcgagacc                                                    858
```

<210> SEQ ID NO 34
<211> LENGTH: 1473
<212> TYPE: DNA
<213> ORGANISM: artificial sequence
<220> FEATURE:
<223> OTHER INFORMATION: Coding sequence

<400> SEQUENCE: 34

```
ggtctcaaat gcctgactat gacaattaca ctacgccatt gtcttctaga tatgcctcca        60
aggaaatgtc agcaacgttt tctttgagaa acagattttc cacatggaga aaactatggt       120
taaatttggc tattgctgag aaggaattgg gcttaactgt tgttacagat gaagcaattg       180
agcaaatgcg caaacacgtc gaaatcactg atgatgaaat cgcaaaagct tctgctcaag       240
aagccattgt aagacatgat gttatggcac atgttcatac atttggtgaa acttgtccgg       300
ctgctgcggg tatcattcac ttaggtgcta cttcctgttt cgttacagac aatgctgatc       360
```

```
taatctttat tagggacgcc tacgatatta ttattccaaa acttgttaac gtcatcaaca      420
gattggctaa gtttgctatg gaatacaagg atttgcctgt attgggttgg actcactttc      480
aaccagcaca attaacgacc ttgggtaaga gagctacttt atggatacaa gagctattgt      540
gggatttgag aaactttgaa agagctagaa acgatatcgg tctacgtggt gttaagggta      600
ctactggtac tcaggcatca ttcttggcct tattccatgg taatcatgat aaagttgaag      660
cccttgacga aagagtaact gaattattag gtttcgataa ggtatatcca gtcactggtc      720
aaacctactc aagaaaaatt gacattgacg tgttggctcc tttgtcttct tttgctgcta      780
ctgcacacaa aatggctact gacataagat tattagccaa cctgaaggaa gttgaggaac      840
cttttgagaa atcacaaatc ggatcctctg ctatggctta caagagaaac ccaatgcgtt      900
gtgagagagt gtgctccttg gctagacact taggttcctt gtttagtgac gccgttcaaa      960
ctgcatccgt tcaatggttc gaaagaactc tggatgattc tgctattaga agaatttctt     1020
taccaagtgc attttaacc gcagatattc tattatctac tttgttgaac atctcatccg     1080
gtttagttgt gtatccaaag gttatcgaaa ggagaattaa gggtgaacta ccttttatgg     1140
ctactgaaaa tatcatcatg gctatggtag aaaagaatgc ctccagacaa gaagtacatg     1200
agcgtattag agtgctctct catcaagccg cagcagtagt caaggaagaa ggtggggaaa     1260
atgatttaat tgaacgagta aagagggatg aattttttcaa gcctatctgg gaagaattag     1320
attctttact ggaaccatcc acttttgttg gtagagctcc acaacaagtt gagaaatttg     1380
ttcaaaaaga cgttaacaat gctttacaac cttttccaaaa gtacctaaac gatgaacaag     1440
tcaagttaaa tgtttgagcg agacctatgc cgt                                  1473

<210> SEQ ID NO 35
<211> LENGTH: 1170
<212> TYPE: DNA
<213> ORGANISM: artificial sequence
<220> FEATURE:
<223> OTHER INFORMATION: Coding sequence

<400> SEQUENCE: 35
ggtctcaaat gaagccggaa gttgagcaag aattagctca tattttgcta actgaattgt       60
tagcttatca atttgcctct cctgtgagat ggattgaaac tcaagatgtt ttttttgaagg     120 attttaacac tgaaagggtt gttgaaatcg gtccttctcc aacttggct gggatggctc      180 aaagaacctt gaagaataaa tacgaatctt acgatgctgc tctgtcttta catagagaaa      240
tcttatgcta ttcgaaggat gccaaagaga tttattatac cccagatcca tccgaactag      300
ctgcaaagga gagcccgct aaggaagaag ctcctgctcc aactccagct gctagtgctc        360
ctgctcctgc agcagcagcc ccagctcccg tcgcggcagc agcccagct gcagcagctg        420 ctgagattgc cgatgaacct gtcaaggctt ccctattgtt gcacgttttg gttgctcaca       480
agttgaagaa gtcgttagat tccattccaa tgtccaagac aatcaaagac ttggtcggtg      540
gtaaatctac agtccaaaat gaatttttgg gtgatttagg taaagaattt ggtactactc      600
ctgaaaaacc agaagaaact ccattagaag aattggcaga aactttccaa gatacccttct     660 ctggagcatt gggtaagcaa tcttcctcgt tattatcaag attaatctca tctaagatgc      720
ctggtgggtt tactattact gtcgctagaa aatacttaca aactcgctgg ggactaccat      780
ctggtagaca agatggtgtc cttttggtag ctttatctaa cgagcctgct gctcgtctag      840
gttctgaagc tgatgccaag gctttcttgg actccatggc tcaaaaatac gcttccattg      900
ttggtgttga cttatcatca gctgctagcg ctagtggtgc tgccggtgca ggtgctgctg      960
```

```
ccggtgcagc tatgatcgat gctggcgctc tggaagaaat aaccaaagac cacaaggttt    1020
tggcgcgtca acaactgcaa gtattggctc gttatctaaa aatggacttg gataacggtg    1080
aaagaaagtt cttgaaagaa aaggacactg ttgctgaact tcaagctcag ttggattact    1140
tgaatgccga attaggtgaa ttctgagacc                                     1170

<210> SEQ ID NO 36
<211> LENGTH: 1374
<212> TYPE: DNA
<213> ORGANISM: artificial sequence
<220> FEATURE:
<223> OTHER INFORMATION: Coding sequence

<400> SEQUENCE: 36
ggtctcaatt ctttgttaac ggtgttgcta cttctttctc tagaaaaaag gccagaacct      60
tcgattcttc ctggaactgg gctaaacaat ctttattatc attatacttt gagataattc     120
atggtgtctt gaaaacgtt gatagagagg ttgttagtga agctatcaat atcatgaaca      180
gatctaacga tgctttgatt aaattcatgg aataccatat ctctaacact gatgaaacaa     240
aaggtgaaaa ctatcaattg gttaaaactc ttggtgagca gttgattgaa actgtaaac     300 aagttttgga tgttgatcca gtttacaaag atgttgctaa gcctaccggt ccaaaaactg     360
ctattgacaa gaacggtaac attacatact cagaagagcc aagagaaaag gttaggaaat     420
tatctcaata cgtacaagaa atggcccttg gtggtccaat caccaaagaa tctcaaccta     480
ctattgaaga ggatttgact cgtgtttaca aggcaatcag tgctcaagct gataaacaag     540
atatttccag ctccaccagg gttgaatttg aaaaactata tagtgatttg atgaagttct     600
tggaaagctc caaagaaatc gatccttctc aaacaaccca attggccggt atggatgttg     660
aggatgcttt ggacaaagat tccaccaaag aagttgcttc tttgccaaac aaatctacca     720
tttctaagac ggtatcttca actattccaa gagaaactat tccgttctta catttgagaa     780
agaagactcc tgccggagat tggaaatatg accgccaatt gtcttctctt ttcttagatg     840
gtttagaaaa ggctgccttc aacggtgtca ccttcaagga caaatacgtc ttgatcactg     900
gtgctggtaa gggttctatt ggtgctgaag tcttgcaagg tttgttacaa ggtggtgcta     960
aggttgttgt taccacctct cgtttctcta agcaagttac agactactac caatccattt    1020
acgccaaata tggtgctaag ggttctactt tgattgttgt tccattcaac caaggttcta    1080
agcaagacgt tgaagctttg attgaattta tctacgacac tgaaaagaat ggtggtttag    1140
gttgggatct agatgctatt attccattcg cggccattcc agaacaaggt attgaattag    1200
aacatattga ttctaagtct gaatttgctc atagaatcat gttgaccaat atcttaagaa    1260
tgatgggttg tgtcaagaag caaaaatctg caagaggtat tgaaacaaga ccagctcaag    1320
tcattctacc aatgtctcca aaccatggta ctttcggtgg tgatggttga gacc           1374

<210> SEQ ID NO 37
<211> LENGTH: 1165
<212> TYPE: DNA
<213> ORGANISM: artificial sequence
<220> FEATURE:
<223> OTHER INFORMATION: Coding sequence

<400> SEQUENCE: 37
ggtctcatgg tatgtattca gaatccaagt gtctttgga acttttgttc aacagatggc      60
actctgaatc ctgggccaat caattaaccg tttgcggtgc tattattggt tggactagag    120
```

```
gtactggttt aatgagcgct aataacatca ttgctgaagg cattgaaaag atgggtgttc      180
gtactttctc tcaaaaggaa atggctttca acttattggg tctattgact ccagaagtcg      240
tagaattgtg ccaaaaatca cctgttatgg ctgacttgaa tggtggtttg caatttgttc      300
ctgaattgaa ggaattcact gctaaattgc gtaaagagtt ggttgaaact tctgaagtta      360
gaaaggcagt ttccatcgaa actgctttgg agcataaggt tgtcaatggc aatagcgctg      420
atgctgcata tgctcaagtc gaaattcaac caagagctaa cattcaactg gacttcccag      480
aattgaaacc atacaaacag gttaaacaaa ttgctcccgc tgagcttgaa ggtttgttgg      540
atttggaaag agttattgta gttaccggtt tgctgaagt cggcccatgg ggttcggcca      600
gaacaagatg ggaaatggaa gcttttggtg aattttcgtt ggaaggttgc gttgaaatgg      660
cctggattat gggcttcatt tcataccata acggtaattt gaagggtcgt ccatacactg      720
gttgggttga ttccaaaaca aaagaaccag ttgatgacaa ggacgttaag gccaagtatg      780
aaacatcaat cctagaacac agtggtatca gattgatcga accagagtta ttcaatggtt      840
acaacccaga aaagaaggaa atgattcaag aagtcattgt cgaagaagac ttggaaccat      900
ttgaggcttc gaaggaaact gccgaacaat ttaaacacca acatggtgac aaagtggata      960
tcttcgaaat cccagaaaca ggagagtact ctgttaagtt actaaagggt gccactttat     1020
acattccaaa ggctttgaga tttgaccgtt tggttgcagg tcaaattcca actggttgga     1080
atgctaagac ttatggtatc tctgatgata tcatttctca ggttgaccca atcacattat     1140
tcgttctcgt ctctgttgtg agacc                                            1165
```

<210> SEQ ID NO 38
<211> LENGTH: 988
<212> TYPE: DNA
<213> ORGANISM: artificial sequence
<220> FEATURE:
<223> OTHER INFORMATION: Coding sequence

<400> SEQUENCE: 38

```
ggtctctgtt gtggaagcat ttattgcatc tggtatcacc gacccatacg aaatgtacaa       60
atacgtacat gttttctgagg ttggtaactg ttctggttct ggtatgggtg gtgtttctgc      120
cttacgtggt atgtttaagg accgtttcaa ggatgagcct gtccaaaatg atattttaca      180
agaatcattt atcaacacca tgtccgcttg ggttaatatg ttgttgattt cctcatctgg      240
tccaatcaag acacctgttg gtgcctgtgc cacatccgtg aatctgttg acattggtgt      300 agaaaccatc ttgtctggta aggctagaat ctgtattgtc ggtggttacg atgatttcca      360
agaagaaggc tcctttgagt tcggtaacat gaaggccact tccaacactt tggaagaatt      420
tgaacatggt cgtaccccag cggaaatgtc cagacctgcc accactaccc gtaacgtttt      480
tatggaagct caaggtgctg gtattcaaat catcatgcaa gctgatttag ctttgaagat      540
gggtgtgcca atttacgtta ttgttgccat ggctgctacc gccaccgata agattggtag      600
atctgtgcca gctccaggta agggtatttt aaccactgct cgtgaacacc actccagtgt      660
taagtatgct tcaccaaaact tgaacatgaa gtacagaaag cgccaattgg ttactcgtga      720
agctcagatt aaagattggg tagaaaacga attggaagct ttgaagttgg aggccgaaga      780
aattccaagc gaagaccaaa acgagttctt acttgaacgt accagagaaa tccacaacga      840
agctgaaagt caattgagag ctgcacaaca acaatggggt aacgacttct acaagaggga      900
cccacgtatt gctccattga gaggagcact ggctacttac ggtttaacta ttgatgactt      960
gggtgtcgct tcattccacg gtgagacc                                          988
```

<210> SEQ ID NO 39
<211> LENGTH: 1063
<212> TYPE: DNA
<213> ORGANISM: artificial sequence
<220> FEATURE:
<223> OTHER INFORMATION: Coding sequence

<400> SEQUENCE: 39

| | | | | | |
|---|---|---|---|---|---|
| ggtctcaacg | gtacatccac | aaaggctaat | gacaagaacg | aatctgccac | aattaatgaa | 60 |
| atgatgaagc | atttgggtag | atctgaaggt | aatcccgtca | ttggtgtttt | ccaaaagttc | 120 |
| ttgactggtc | atccaaaggg | tgctgctggt | gcatggatga | tgaatggtgc | tttgcaaatt | 180 |
| ctaaacagtg | gtattattcc | aggtaaccgt | aacgctgata | acgtggataa | gatcttggag | 240 |
| caatttgaat | acgtcttgta | cccatccaag | actttaaaga | ccgacggtgt | cagagccgtg | 300 |
| tccatcactt | ctttcggttt | tggtcaaaag | ggtggtcaag | ctattgtggt | tcatccagac | 360 |
| tacttatacg | gtgctatcac | tgaagacaga | tacaacgagt | atgtcgccaa | ggttagtgcc | 420 |
| agagagaaaa | gtgcctacaa | attcttccat | aatggtatga | tctacaacaa | gttgttcgta | 480 |
| agtaaagagc | atgctccata | cactgatgaa | ttggaagagg | atgtttactt | ggacccatta | 540 |
| gcccgtgtat | ctaaggataa | gaaatcaggc | tccttgactt | tcaactctaa | aaacatccaa | 600 |
| agcaaggaca | gttacatcaa | tgctaacacc | attgaaactg | ccaagatgat | tgaaaacatg | 660 |
| accaaggaga | agtctctaa | cggtggcgtc | ggtgtagatg | ttgaattaat | cactagcatc | 720 |
| aacgttgaaa | atgatacttt | tatcgagcgc | aatttcaccc | cgcaagaaat | agagtactgc | 780 |
| agcgcgcagc | ctagtgtgca | aagctctttc | gctgggacat | ggtccgccaa | agaggctgtt | 840 |
| ttcaagtcct | taggcgtcaa | gtccttaggc | ggtggtgctg | cattgaaaga | catcgaaatc | 900 |
| gtacgcgtta | acaaaaacgc | tccagccgtt | gaactgcacg | gtaacgccaa | aaaggctgcc | 960 |
| gaagaagctg | gtgttaccga | tgtgaaggta | tctatttctc | acgatgacct | ccaagctgtc | 1020 |
| gcggtcgccg | tttctactaa | gaaatgagcg | agacctatgc | cgt | | 1063 |

<210> SEQ ID NO 40
<211> LENGTH: 522
<212> TYPE: DNA
<213> ORGANISM: artificial sequence
<220> FEATURE:
<223> OTHER INFORMATION: Terminal tag

<400> SEQUENCE: 40

| | | | | | |
|---|---|---|---|---|---|
| ggtctcacag | ttcgtttatc | cttttttgaac | tgcatctggc | atcgttaaca | gtaaggccat | 60 |
| ctggaacatc | aagcaagcac | tccacttta | cgtcacaacc | atagttggtt | aactaagaaa | 120 |
| agacagtaca | tatttccctt | ccgagtcact | tattttttt | ttcttctgaa | aaaattaatt | 180 |
| agattaattt | caattaatat | catttccgct | tatctgactt | ctttcatttt | ttttctctat | 240 |
| atttcgcgtt | tactaggaaa | gaaaaggaaa | aaaaatttt | ccccctccat | ctgtcccaaa | 300 |
| tcgggtagcg | atgagctgct | atagaatttt | ctatttaaac | atgtttgata | agcccaattt | 360 |
| ccgttagatt | ttgttccccc | ttcgcagttt | ggtttgccgt | aacttttta | ttttagtctc | 420 |
| catctagctg | gagtaatacg | atgtagtgcc | ttgtaatctt | tcttatttt | atattaccgt | 480 |
| tcgtgttcat | tatatccatt | acgttcccat | aaatgcgaga | cc | | 522 |

<210> SEQ ID NO 41
<211> LENGTH: 222
<212> TYPE: DNA

<213> ORGANISM: artificial sequence
<220> FEATURE:
<223> OTHER INFORMATION: Vector tag

<400> SEQUENCE: 41

```
ggtctcatga gtagacatat catatccttc agtaacttga atcatacagc agaatttgta      60
caatagacaa cgcatataac tgcgaccata tgtatacgta taactaatta ttatctcaaa     120
gtttattccc ttagcctcac cggtaacctg tgaggcgcga ttacgttttc cctctgttca     180
ccaccacgta acgcgatatt tgacacatac gttttcgaga cc                         222
```

<210> SEQ ID NO 42
<211> LENGTH: 690
<212> TYPE: DNA
<213> ORGANISM: artificial sequence
<220> FEATURE:
<223> OTHER INFORMATION: Vector tag

<400> SEQUENCE: 42

```
ggtctcaaat gtcggcaaac gataagcaat acatctcgta caacaacgta catcaactat      60
gtcaagtatc cgctgagaga attaagaatt tcaagccgga cttaatcatt gccattggtg     120
gtggtggttt cattcctgct aggatcctac gtacgttcct aaaggagccc ggcgtgccaa     180
ccatcagaat ttttgctatt attttgtctt tgtacgaaga tttgaacagt gtaggctcag     240
aagttgagga agttggtgtt aaggttagca gaacacaatg gattgattac gagcaatgta     300
aattagatct agtcggcaag aacgttctta tcgttgacga agtcgatgac acccgtacca     360
cacttcatta cgctttgagt gaattggaaa aggatgcagc tgaacaggca aaggctaaag     420
gtatcgatac tgaaaagtct ccagagatga aacaaacttc gggattttt gttctacacg      480
ataagcaaaa accaaagaaa gcagatttgc ctgccgaaat gttgaatgac aagaaccgtt     540
attttgcagc taaaactgtt ccagacaagt ggtatgcata tccatgggaa tctactgaca     600
ttgtttttcca tactagaatg gctattgaac agggcaatga catctttatt cctgagcagg     660
aacacaagca atgagcgaga cctatgccgt                                        690
```

<210> SEQ ID NO 43
<211> LENGTH: 744
<212> TYPE: DNA
<213> ORGANISM: artificial sequence
<220> FEATURE:
<223> OTHER INFORMATION: Green fluorescent protein tag

<400> SEQUENCE: 43

```
ggtctcagga tcaatggtga gcaagggcga ggagctgttc accggggtgg tgcccatcct      60
ggtcgagctg gacggcgacg taaacggcca agttcagc gtgagggcg aaggcgaggg       120
cgatgccacc aacggcaagc tgaccctgaa gttcatctgc accaccggca agctgcccgt     180
gcccctggccc cccctcgtga ccaccttgac ctacggcgtg cagtgcttcg cccgctaccc     240
cgaccacatg aagcagcacg acttcttcaa gtccgccatg cccgaaggct acgtccagga     300
gcgcaccatc ttcttcaagg acgacggcac ctacaagacc cgcgccgagg tgaagttcga     360
gggcgacacc ctggtgaacc gcatcgagct gaagggcatc gacttcaagg aggacggcaa     420
catcctgggg cacaagctgg agtacaacta caacagccac aaggtctata tcaccgccga     480
caagcagaag aacggcatca aggtgaactt caagatccgc cacaacgtgg aggacggcag     540
cgtgcagctc gccgaccact accagcagaa caccccatc ggcgacgcc ccgtgctgct       600
gcccgacaac cactacctga gcacccagtc cgtgctgagc aaagacccca acgagaagcg     660
```

```
cgatcacatg gtcctgctgg agttcgtgac cgccgccggg atcactctcg gcatggacga    720
gctgtacaag taatgagcga gacc                                          744
```

<210> SEQ ID NO 44
<211> LENGTH: 735
<212> TYPE: DNA
<213> ORGANISM: artificial sequence
<220> FEATURE:
<223> OTHER INFORMATION: M Cherry tag

<400> SEQUENCE: 44

```
ggtctcagga tcaatggtga gcaagggcga ggaggataac atggccatca tcaaggagtt     60
catgcgcttc aaggtgcaca tggagggctc cgtgaacggc cacgagttcg agatcgaggg    120
cgagggcgag ggccgcccct acgagggcac ccagaccgcc aagctgaagg tgaccaaggg    180
tggccccctg cccttcgcct gggacatcct gtcccctcag ttcatgtacg gctccaaggc    240
ctacgtgaag caccccgccg acatccccga ctacttgaag ctgtccttcc ccgagggctt    300
caagtgggag cgcgtgatga acttcgagga cggcggcgtg gtgaccgtga cccaggactc    360
ctccctgcag gacggcgagt tcatctacaa ggtgaagctg cgcggcacca acttcccctc    420
cgacggcccc gtaatgcaga gaagaccat gggctgggag gcctcctccg agcggatgta    480
ccccgaggac ggcgccctga agggcgagat caagcagagg ctgaagctga aggacggcgg    540
ccactacgac gctgaggtca agaccaccta caaggccaag aagcccgtgc agctgcccgg    600
cgcctacaac gtcaacatca gttggacat cacctcccac aacgaggact acaccatcgt    660
ggaacagtac gaacgcgccg agggccgcca ctccaccggc ggcatggacg agctgtacaa    720
gtaatgagcg agacc                                                   735
```

<210> SEQ ID NO 45
<211> LENGTH: 45
<212> TYPE: DNA
<213> ORGANISM: artificial sequence
<220> FEATURE:
<223> OTHER INFORMATION: Oligonucleotide

<400> SEQUENCE: 45

```
tgtggtaagc ctatccctaa ccctctcctc ggactcgatt ctacg              45
```

<210> SEQ ID NO 46
<211> LENGTH: 47
<212> TYPE: DNA
<213> ORGANISM: artificial sequence
<220> FEATURE:
<223> OTHER INFORMATION: Oligonucleotide

<400> SEQUENCE: 46

```
taggcgtaga atcgagtccg aggagagggt tagggatagg cttacca             47
```

<210> SEQ ID NO 47
<211> LENGTH: 32
<212> TYPE: DNA
<213> ORGANISM: artificial sequence
<220> FEATURE:
<223> OTHER INFORMATION: Primer

<400> SEQUENCE: 47

```
agaactttgg aggaagagac catgggccgc cc                             32
```

<210> SEQ ID NO 48

```
<211> LENGTH: 32
<212> TYPE: DNA
<213> ORGANISM: artificial sequence
<220> FEATURE:
<223> OTHER INFORMATION: Primer

<400> SEQUENCE: 48
gggcggccca tggtctcttc ctccaaagtt ct                         32

<210> SEQ ID NO 49
<211> LENGTH: 21
<212> TYPE: DNA
<213> ORGANISM: artificial sequence
<220> FEATURE:
<223> OTHER INFORMATION: DNA fragment

<400> SEQUENCE: 49
agaactttgg aggaagagac c                                     21

<210> SEQ ID NO 50
<211> LENGTH: 21
<212> TYPE: DNA
<213> ORGANISM: artificial sequence
<220> FEATURE:
<223> OTHER INFORMATION: Primer

<400> SEQUENCE: 50
ggtctcttcc tccaaagttc t                                     21

<210> SEQ ID NO 51
<211> LENGTH: 29
<212> TYPE: DNA
<213> ORGANISM: artificial sequence
<220> FEATURE:
<223> OTHER INFORMATION: DNA fragment

<400> SEQUENCE: 51
ggtctcaagg aaaagaccat gggccgccc                             29

<210> SEQ ID NO 52
<211> LENGTH: 29
<212> TYPE: DNA
<213> ORGANISM: artificial sequence
<220> FEATURE:
<223> OTHER INFORMATION: DNA fragment

<400> SEQUENCE: 52
gggcggccca tggtcttttc cttgagacc                             29

<210> SEQ ID NO 53
<211> LENGTH: 32
<212> TYPE: DNA
<213> ORGANISM: artificial sequence
<220> FEATURE:
<223> OTHER INFORMATION: DNA fragment

<400> SEQUENCE: 53
agaactttgg aggaaaagac catgggccgc cc                         32

<210> SEQ ID NO 54
<211> LENGTH: 32
```

```
-continued

<212> TYPE: DNA
<213> ORGANISM: artificial sequence
<220> FEATURE:
<223> OTHER INFORMATION: DNA fragment

<400> SEQUENCE: 54
gggcggccca tggtcttttc ctccaaagtt ct                                32
```